(12) United States Patent
Austad et al.

(10) Patent No.: US 9,238,672 B2
(45) Date of Patent: Jan. 19, 2016

(54) METHODS FOR STEREOSELECTIVE REDUCTION

(71) Applicant: INFINITY PHARMACEUTICALS, INC., Cambridge, MA (US)

(72) Inventors: Brian C. Austad, Tewksbury, MA (US); Andre Lescarbeau, Somerville, MA (US); Lin-Chen Yu, Quincy, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 14/268,952

(22) Filed: May 2, 2014

(65) Prior Publication Data
US 2014/0357868 A1 Dec. 4, 2014

Related U.S. Application Data

(63) Continuation of application No. 12/810,600, filed as application No. PCT/US2008/088302 on Dec. 24, 2008, now Pat. No. 8,716,479, which is a continuation-in-part of application No. 11/965,688, filed on Dec. 27, 2007, now Pat. No. 7,812,164.

(60) Provisional application No. 61/017,162, filed on Dec. 27, 2007.

(51) Int. Cl.
| | | |
|---|---|---|
| C07D 471/00 | (2006.01) |
| C07J 7/00 | (2006.01) |
| C07D 471/10 | (2006.01) |
| C07J 1/00 | (2006.01) |
| C07J 5/00 | (2006.01) |
| C07J 9/00 | (2006.01) |
| C07J 21/00 | (2006.01) |
| C07J 43/00 | (2006.01) |
| C07J 65/00 | (2006.01) |
| C07J 69/00 | (2006.01) |
| C07J 71/00 | (2006.01) |
| C07D 491/22 | (2006.01) |

(52) U.S. Cl.
CPC ............... *C07J 7/009* (2013.01); *C07D 471/10* (2013.01); *C07D 491/22* (2013.01); *C07J 1/0011* (2013.01); *C07J 5/0053* (2013.01); *C07J 9/00* (2013.01); *C07J 21/00* (2013.01); *C07J 43/006* (2013.01); *C07J 65/00* (2013.01); *C07J 69/00* (2013.01); *C07J 71/0005* (2013.01); *C07B 2200/09* (2013.01)

(58) Field of Classification Search
CPC .................................................... C07D 471/10
USPC ........................................................ 546/17
See application file for complete search history.

(56) References Cited

U.S. PATENT DOCUMENTS

| | | |
|---|---|---|
| 4,968,787 A | 11/1990 | Inada et al. |
| 5,086,047 A | 2/1992 | Gourvest et al. |
| 5,169,780 A | 12/1992 | Stirling et al. |
| 5,378,475 A | 1/1995 | Smith et al. |
| 6,177,407 B1 | 1/2001 | Rodgers et al. |
| 6,184,381 B1 | 2/2001 | Ikariya et al. |
| 6,238,876 B1 | 5/2001 | Altaba |
| 6,291,516 B1 | 9/2001 | Dudek et al. |
| 6,372,931 B1 | 4/2002 | Blacker et al. |
| 6,432,970 B2 | 8/2002 | Beachy et al. |
| 6,509,467 B1 | 1/2003 | Blacker et al. |
| 6,545,188 B2 | 4/2003 | Blacker et al. |
| 6,613,798 B1 | 9/2003 | Porter et al. |
| 6,686,388 B2 | 2/2004 | Dudek et al. |
| 6,867,216 B1 | 3/2005 | Beachy et al. |
| 6,887,820 B1 | 5/2005 | Ikariya et al. |
| 6,909,003 B2 | 6/2005 | Storz |
| 7,098,196 B1 | 8/2006 | Beachy et al. |
| 7,112,690 B2 | 9/2006 | Chi et al. |
| 7,230,004 B2 | 6/2007 | Adams et al. |
| 7,250,526 B2 | 7/2007 | Blacker et al. |
| 7,291,626 B1 | 11/2007 | Beachy et al. |
| 7,407,967 B2 | 8/2008 | Adams et al. |
| 7,476,661 B2 | 1/2009 | Beachy et al. |
| 7,541,183 B2 | 6/2009 | Rudnicki et al. |
| 7,605,167 B2 | 10/2009 | Tas et al. |
| 7,629,352 B2 | 12/2009 | Tas et al. |
| 7,648,994 B2 | 1/2010 | Castro et al. |
| 7,655,674 B2 | 2/2010 | Beachy et al. |
| 7,812,164 B2 | 10/2010 | Austad et al. |

(Continued)

FOREIGN PATENT DOCUMENTS

| | | |
|---|---|---|
| EP | 0388188 A1 | 9/1990 |
| EP | 0434570 A2 | 6/1991 |

(Continued)

OTHER PUBLICATIONS

Aboulkassim et al., "Alteration of the PATCHED locus in superficial bladder cancer", Oncogene, vol. 22, No. 19, pp. 2967-2971 (2003).

(Continued)

*Primary Examiner* — Andrew D Kosar
*Assistant Examiner* — Raymond Covington
(74) *Attorney, Agent, or Firm* — Susan T. Evans; McDermott Will & Emery LLP

(57) ABSTRACT

The invention is directed to a method to reduce a C—C double bond of an enone of a steroidal compound to produce a mixture of β ketone product and α ketone product, comprising treating a solution or suspension of the steroidal compound in a solvent with hydrogen gas in the presence of a catalyst and a substituted pyridine.

24 Claims, No Drawings

(56) References Cited

U.S. PATENT DOCUMENTS

| | | |
|---|---|---|
| 7,867,492 B2 | 1/2011 | Beachy et al. |
| 7,875,628 B2 | 1/2011 | Adams et al. |
| 7,893,078 B2 | 2/2011 | Tas et al. |
| 7,964,590 B2 | 6/2011 | Castro et al. |
| 7,994,191 B2 | 8/2011 | Castro et al. |
| 8,017,648 B2 | 9/2011 | Castro et al. |
| 8,227,509 B2 | 7/2012 | Castro et al. |
| 8,236,956 B2 | 8/2012 | Adams et al. |
| 8,293,760 B2 | 10/2012 | Castro et al. |
| 8,426,436 B2 | 4/2013 | Castro et al. |
| 8,431,566 B2 | 4/2013 | Castro et al. |
| 8,669,365 B2 | 3/2014 | Austad et al. |
| 8,703,448 B2 | 4/2014 | Austad et al. |
| 8,716,479 B2 | 5/2014 | Austad et al. |
| 2002/0006931 A1 | 1/2002 | Beachy et al. |
| 2002/0087258 A1 | 7/2002 | Johnson |
| 2002/0193347 A1 | 12/2002 | Bulliard et al. |
| 2003/0114393 A1 | 6/2003 | Liscovitch et al. |
| 2003/0162870 A1 | 8/2003 | Kimura et al. |
| 2003/0175355 A1 | 9/2003 | Tobyn et al. |
| 2003/0220314 A1 | 11/2003 | Shackleton et al. |
| 2004/0023949 A1 | 2/2004 | Baxter et al. |
| 2004/0072913 A1 | 4/2004 | Tas et al. |
| 2004/0072914 A1 | 4/2004 | Tas et al. |
| 2004/0073404 A1 | 4/2004 | Brooks et al. |
| 2004/0110663 A1 | 6/2004 | Dudek et al. |
| 2004/0126359 A1 | 7/2004 | Lamb et al. |
| 2004/0127474 A1 | 7/2004 | Dudek et al. |
| 2004/0247643 A1 | 12/2004 | Martinod et al. |
| 2005/0049218 A1 | 3/2005 | Gilbertson |
| 2005/0112707 A1 | 5/2005 | Altaba et al. |
| 2005/0203061 A1 | 9/2005 | Yamashita et al. |
| 2006/0020020 A1 | 1/2006 | Dudek et al. |
| 2006/0074030 A1 | 4/2006 | Adams et al. |
| 2006/0094660 A1 | 5/2006 | Thomson |
| 2006/0128639 A1 | 6/2006 | Beachy |
| 2006/0142245 A1 | 6/2006 | Beachy et al. |
| 2006/0252073 A1 | 11/2006 | Yilmaz et al. |
| 2007/0003550 A1 | 1/2007 | Antonia et al. |
| 2007/0009530 A1 | 1/2007 | Altaba et al. |
| 2007/0021493 A1 | 1/2007 | Guicherit et al. |
| 2007/0036800 A1 | 2/2007 | Bergstein |
| 2007/0060546 A1 | 3/2007 | Ruat et al. |
| 2007/0179091 A1 | 8/2007 | De Sauvage et al. |
| 2007/0191410 A1 | 8/2007 | Adams et al. |
| 2007/0219250 A1 | 9/2007 | Singh et al. |
| 2007/0231828 A1 | 10/2007 | Beachy et al. |
| 2007/0281040 A1 | 12/2007 | Weichselbaum et al. |
| 2008/0019961 A1 | 1/2008 | Wicha et al. |
| 2008/0057071 A1 | 3/2008 | Watkins et al. |
| 2008/0058298 A1 | 3/2008 | Beachy et al. |
| 2008/0089915 A1 | 4/2008 | Tas et al. |
| 2008/0095761 A1 | 4/2008 | Beachy et al. |
| 2008/0107749 A1 | 5/2008 | Maitra et al. |
| 2008/0118493 A1 | 5/2008 | Beachy et al. |
| 2008/0138379 A1 | 6/2008 | Jennings-Spring |
| 2008/0182859 A1 | 7/2008 | Brunton et al. |
| 2008/0255059 A1 | 10/2008 | Beachy et al. |
| 2008/0262051 A1 | 10/2008 | Balkovec et al. |
| 2008/0269182 A1 | 10/2008 | Pluda et al. |
| 2008/0269272 A1 | 10/2008 | Adams et al. |
| 2008/0287420 A1 | 11/2008 | Castro et al. |
| 2008/0293754 A1 | 11/2008 | Austad et al. |
| 2008/0293755 A1 | 11/2008 | Castro et al. |
| 2009/0012109 A1 | 1/2009 | Austad et al. |
| 2009/0181997 A1 | 7/2009 | Grayzel et al. |
| 2009/0208579 A1 | 8/2009 | Ueki et al. |
| 2009/0216022 A1 | 8/2009 | Austad et al. |
| 2009/0263317 A1 | 10/2009 | Chen et al. |
| 2009/0286822 A1 | 11/2009 | Tas et al. |
| 2009/0305338 A1 | 12/2009 | Ritala-Nurmi et al. |
| 2010/0003728 A1 | 1/2010 | Jayatilake et al. |
| 2010/0093625 A1 | 4/2010 | Tarasova et al. |
| 2010/0099116 A1 | 4/2010 | Faia et al. |
| 2010/0144775 A1 | 6/2010 | Castro et al. |
| 2010/0210515 A1 | 8/2010 | Nash et al. |
| 2010/0222287 A1 | 9/2010 | McGovern et al. |
| 2010/0273818 A1 | 10/2010 | Beachy et al. |
| 2010/0286114 A1 | 11/2010 | Thomas et al. |
| 2010/0286180 A1 | 11/2010 | Castro et al. |
| 2010/0297118 A1 | 11/2010 | MacDougall et al. |
| 2011/0009442 A1 | 1/2011 | Austad et al. |
| 2011/0034498 A1 | 2/2011 | McGovern et al. |
| 2011/0104254 A1 | 5/2011 | Tas et al. |
| 2011/0135739 A1 | 6/2011 | Carter et al. |
| 2011/0166353 A1 | 7/2011 | Adams et al. |
| 2011/0183948 A1 | 7/2011 | Levine et al. |
| 2011/0230509 A1 | 9/2011 | Castro et al. |
| 2012/0010229 A1 | 1/2012 | MacDougall et al. |
| 2012/0010230 A1 | 1/2012 | MacDougall et al. |
| 2012/0015934 A1 | 1/2012 | Castro et al. |
| 2012/0065218 A1 | 3/2012 | Castro et al. |
| 2012/0065399 A1 | 3/2012 | Genov et al. |
| 2012/0065400 A1 | 3/2012 | Genov et al. |
| 2012/0077834 A1 | 3/2012 | Castro et al. |
| 2012/0083484 A1 | 4/2012 | Castro et al. |
| 2012/0083607 A1 | 4/2012 | Austad et al. |
| 2013/0108582 A1 | 5/2013 | Castro et al. |
| 2013/0108583 A1 | 5/2013 | Castro et al. |
| 2014/0107142 A1 | 4/2014 | Castro et al. |

FOREIGN PATENT DOCUMENTS

| | | |
|---|---|---|
| EP | 2225254 A2 | 9/2010 |
| EP | 2443926 A2 | 4/2012 |
| JP | 2010-0514796 A | 5/2010 |
| WO | WO 94/20520 A1 | 9/1994 |
| WO | WO 95/18856 A1 | 7/1995 |
| WO | WO 96/17924 A2 | 6/1996 |
| WO | WO 00/18708 A1 | 4/2000 |
| WO | WO 00/41545 A2 | 7/2000 |
| WO | WO 01/09077 A1 | 2/2001 |
| WO | WO 01/19800 A2 | 3/2001 |
| WO | WO 01/26644 A2 | 4/2001 |
| WO | WO 01/27135 A3 | 4/2001 |
| WO | WO 01/49279 A2 | 7/2001 |
| WO | WO 01/74344 A2 | 10/2001 |
| WO | WO 01/90077 A1 | 11/2001 |
| WO | WO 02/30462 A2 | 4/2002 |
| WO | WO 02/078703 A1 | 10/2002 |
| WO | WO 02/078704 A1 | 10/2002 |
| WO | WO 03/011219 A2 | 2/2003 |
| WO | WO 03/088964 A1 | 10/2003 |
| WO | WO 03/088970 A2 | 10/2003 |
| WO | WO 2004/020599 A2 | 3/2004 |
| WO | WO 2005/013800 A2 | 2/2005 |
| WO | WO 2005/032343 A2 | 4/2005 |
| WO | WO 2005/033288 A2 | 4/2005 |
| WO | WO 2005/042700 A2 | 5/2005 |
| WO | WO 2006/026430 A1 | 3/2006 |
| WO | WO 2006/028958 A2 | 3/2006 |
| WO | WO 2006/050351 A2 | 5/2006 |
| WO | WO 2006/078283 A2 | 7/2006 |
| WO | WO 2007/053596 A1 | 5/2007 |
| WO | WO 2007/054623 A2 | 5/2007 |
| WO | WO 2007/059157 A1 | 5/2007 |
| WO | WO 2007/093372 A1 | 8/2007 |
| WO | WO 2007/120827 A2 | 10/2007 |
| WO | WO 2007/123511 A2 | 11/2007 |
| WO | WO 2007/131201 A2 | 11/2007 |
| WO | WO 2008/011071 A1 | 1/2008 |
| WO | WO 2008/037732 A1 | 4/2008 |
| WO | WO 2008/073165 A1 | 5/2008 |
| WO | WO 2008/070357 A2 | 6/2008 |
| WO | WO 2008/083248 A2 | 7/2008 |
| WO | WO 2008/083252 A2 | 7/2008 |
| WO | WO 2008/089123 A2 | 7/2008 |
| WO | WO 2008/109184 A1 | 9/2008 |
| WO | WO 2008/109829 A1 | 9/2008 |
| WO | WO 2008/110611 A1 | 9/2008 |
| WO | WO 2008/112913 A1 | 9/2008 |
| WO | WO 2008/131354 A2 | 10/2008 |
| WO | WO 2009/086416 A1 | 7/2009 |
| WO | WO 2009/086451 A1 | 7/2009 |

(56) References Cited

FOREIGN PATENT DOCUMENTS

| | | |
|---|---|---|
| WO | WO 2009/099625 A2 | 8/2009 |
| WO | WO 2009/126840 A1 | 10/2009 |
| WO | WO 2010/000070 A1 | 1/2010 |
| WO | WO 2010/002970 A2 | 1/2010 |
| WO | WO 2010/085654 A1 | 7/2010 |
| WO | WO 2011/017551 A2 | 2/2011 |
| WO | WO 2011/057222 A2 | 5/2011 |
| WO | WO 2011/063309 A1 | 5/2011 |
| WO | WO 2012/006584 A2 | 1/2012 |
| WO | WO 2012/006589 A2 | 1/2012 |
| WO | WO 2012/037217 A1 | 3/2012 |

OTHER PUBLICATIONS

Ailles and Siu, "Targeting the hedgehog pathway in cancer: can the spines be smoothened?", Clin. Cancer Res.; vol. 17, No. 8, pp. 2071-2073 (2011).
Alexandre et al., "Transcriptional activation of hedgehog target genes in Drosophila is mediated directly by the Cubitus interruptus protein, a member of the GLI family of zinc finger DNA-binding proteins", Genes Dev., vol. 10, pp. 2003-2013 (1996).
Athar et al., "Hedgehog signaling in skin development and cancer", Exp. Dermatol., vol. 15, No. 9, pp. 667-677 (2006).
Bailey et al., "Sonic hedgehog promotes desmoplasia in pancreatic cancer", Clin. Cancer Res., vol. 14, No. 19, pp. 5995-6004 (2008).
Bailey et al., "Sonic hedgehog paracrine signaling regulates metastasis and lymphangiogenesis in pancreatic cancer", Oncogene, vol. 28, No. 40, pp. 3513-3525 (2009).
Bale and Yu, "The hedgehog pathway and basal cell carcinomas", Human Molecular Genetics, vol. 10, No. 7, pp. 757-762 (2001).
Banerjee et al., "Recruitment of the sonic hedgehod signalling cascade in electroconvulsive seizure-mediated regulation of adult rat hippocampal neurogenesis", Eur. J. Neurosci., vol. 22, No. 7, pp. 1570-1580 (2005).
Bar et al., "Cyclopamine-mediated hedgehog pathway inhibition depletes stem-like cancer cells in glioblastoma", Stem Cells, vol. 25, No. 10, pp. 2524-2533 (2007).
Barken et al., "Noscapine inhibits human prostate cancer progression and metastasis in a mouse model," Anticancer Res., vol. 28, No. 6A, pp. 3701-3704 (2008).
Belloni et al., "Identification of Sonic hedgehog as a candidate gene responsible for holoprosencephaly", Nature Genetics, vol. 14, pp. 353-356 (1996).
Berge et al., "Pharmaceutical salts", J. Pharm. Sci., 66, No. 1, pp. 1-19 (1977).
Berger et al., "Regulator of G-protein signaling-5 induction in pericytes coincides with active vessel remodeling during neovascularization," Blood, vol. 105, No. 3, pp. 1094-1101 (2005).
Berman et al., "Medulloblastoma growth inhibiton by hedgehog pathway blockade", Science, vol. 297, pp. 1559-1561 (2002).
Berman et al., "Widespread requirement for Hedgehog ligand stimulation in growth of digestive tract tumours", Nature, vol. 425, pp. 846-851 (2003).
Bhat et al., "Synthesis and biological evaluation of novel steroidal pyrazoles as substrates for bile acid transporters", Bioorg. Med. Chem. Lett., vol. 15, pp. 85-87 (2005).
Bhattacharya et al., "Role of Hedgehog signaling in ovarian cancer", Clin. Cancer Res., vol. 14, No. 23, pp. 7659-7666 (2008).
Biospace, Print News Article, "Infinity Pharmaceuticals, Inc. Announces Hedgehog Pathway Inhibitor Agreement with AstraZeneca PLC (AZN)", Cambridge, Mass., Nov. 12, 2007, (Prime Newswire), 2 pages, Retreived from the internet: http://www.biospace.com/news_story.aspx?NewsEntityId=77067.
Brown and Keeler, "Structure-activity relation of steroid teratogens, 1. Jervine ring system", J. Agric. Food Chem., vol. 26, No. 3, pp. 561-563 (1978).
Brown and Keeler, "Structure-activity relation of steroid teratogens, 2. N-substituted jervines", J. Agric. Food Chem., vol. 26, No. 3, pp. 564-566 (1978).
Browne et al., "Isolation of teratogenic alkaloids by reversed-phase high-performance liquid chromatography" Journal of Chromatography Biomedical Applications, vol. 336, pp. 211-220 (1984).
Business Wire, "Infinity Reports Update from Phase 2 Study of Saridegib Plus Gemcitabine in Patients with Metastatic Pancreatic Cancer", Infinity Pharmaceuticals, 3 pages, Jan. 27, 2012, Retreived from the internet: http://www.businesswire.com/news/home/20120127005146/en/Infinity-Reports-Update-Phase-2-Study-Saridegib#.U3Us_IdV8E.
Campbell et al., "Direct Targeting of the Hedgehog pathway in primary chondrosarcoma xenografts with smoothened Inhibitor IPI-926", Infinity Pharmaceuticals, Inc., Presentation Poster, Abstract #LB380, 1 page (2011).
Carter et al., "Formulation for IPI-926 drug product, a novel oral Hedgehog pathway inhibitor in clincal development", Infinity Pharmaceuticals, Inc., Presentation Poster, Abstract #M1169, with Presentation Abstract, 2 pages (2009).
Caserta et al., "p63 overexpression induces the expression of sonic hedgehog", Mol. Cancer Res., vol. 4, No. 10, pp. 759-768 (2006).
Chaumeil, "Micronization: A method of improving the bioavailability of poorly soluble drugs", Methods Find. Exp. Clin. Pharmacol., vol. 20, No. 3, pp. 211-215 (1998).
Chen et al., "Inhibition of Hedgehog signaling by direct binding of cyclopamine to smoothened", Genes Dev., vol. 16, No. 21, pp. 2743-2748 (2002).
Chen et al., "Small molecule modulation of Smoothened activity", PNAS, vol. 99, No. 22, pp. 14071-14076 (2002).
Chen et al., "Targeting the hedgehog pathway to mitigate treatment resistance", Cell Cycle, vol. 6, Issue. 15, pp. 1826-1830 (2007).
Chen et al., "Sonic hedgehog dependent phosphorylation by CK1α and GRK2 is required for ciliary accumulation and activation of smoothened", PloS Biology, vol. 9, Issue. 6, No. e1001083, 16 pages (2011).
Christiansen et al., "Antiandrogenic steroidal sulfonylpyrazoles", J. Med. Chem., vol. 33, pp. 2094-2100 (1990).
Chung et al., "New Targets for therapy in prostate cancer: modulation of stromal-epithelial interactions", Urology, vol. 62, Suppl. 5A, pp. 44-54 (2003).
Clement et al., "HEDGEHOG-GLI1 signaling regulates human glioma growth, cancer stem cell self-renewal and tumorigenicity", Curr. Biol., vol. 17, No. 2, pp. 165-172 (2007).
Clinton et al., "Steroidal heterocycles, VI. Formulation of A/B-cis 3-Ketosteroids. Preparation of 5βSteroidal[3,2-c]pyrazoles", J. Org. Chem., vol. 27, pp. 2800-2807 (1962).
COMTEX, "Infinity announces hedgehog pathway inhibitor agreement with AstraZeneca", Infinity Pharmaceuticals, PrimeWireNewswire via COMTEX News Network, 2 pages, Nov. 12, 2007, Retrieved from the internet: http://files.shareholder.com/downloads/INFI/0x0x144355/71ecb752-43b2-4a26-9867-8feea13ee93d/INFI_News_2007_11_12_General.pdf.
Cong et al., "Steroidal alkaloids from the roots and rhizomes of Veratrum nigrum L", Helvetica Chimica Acta, vol. 90, Issue 5, pp. 1038-1042 (2007).
Cooper et al., "Teratogen-mediated inhibition of target tissue response to Shh signaling", Science, vol. 280, pp. 1603-1607 (1998).
Corbit et al., "Vertebrate smoothened functions at the primary cilium", Nature, vol. 437 No. 7061, pp. 1018-1021 (2005).
Cutcliffe et al., "Clear cell sarcoma of the kidney: Up-regulation of neural markers with activation of the sonic hedgehog and Akt pathways", Clin. Cancer Res., vol. 11, No. 22, pp. 7986-7994 (2005).
Dakhova et al., "Global gene expression analysis of reactive stroma in prostate cancer", Clin. Cancer Res., vol. 15, No. 12, pp. 3979-3989 (2009).
Dierks et al., "Essential role of stromally induced hedgehog signaling in B-cell malignancies", Nat. Med., vol. 13, No. 8, pp. 944-951 (2007) Pre Publication Article, DOI:10.1038/nm1614 pp. 1-8 (2007).
Dierks et al , "Expansion of Bcr-Abl-positive leukemic stem cells is dependent on Hedgehog pathway activation", Cancer Cell, vol. 14, No. 3, pp. 238-249 (2008).
Di Magliano and Hebrok, "Hedgehog signalling in cancer formation and maintenance", Nat. Rev., vol. 3, No. 12, pp. 903-911 (2003).

(56) References Cited

OTHER PUBLICATIONS

Djerassi and Gutzwiller, "Selective reduction of steroids by homegeneous catalytic hydrogenation", J. Am. Chem. Soc., vol. 88, No. 19, pp. 4537-4538 (1966).
Dormeyer et al., "Plasma membrane proteomics of human embryonic stem cells and human embryonal carcinoma cells", J. Proteome Res., vol. 7, No. 7, pp. 2936-2951 (2008).
Dörwald, "Side reactions in organic synthesis, A guide to successful synthesis design", Wiley-VCH, Verlag GmbH & Co. KGaA, Weinheim, ISBN:3-527-31021-5, p. IX of Preface and pp. 8-13 (2005).
Ehtesham et al., "Ligand-dependent activation of the hedgehog pathway in glioma progenitor cells", Oncogene, vol. 26, No. 39, pp. 5752-5761 (2007).
Engelman and Settleman, "Acquired resistance to tyrosine kinase inhibitors during cancer therapy", Curr, Opin. Genet. Dev., vol. 18, No. 1, pp. 73-79 (2008).
Everaere et al., "Ruthenium (II)-catalyzed asymmetric transfer hydrogenation of carbonyl compounds with 2-propanol and ephedrine-type ligands", Adv. Synth. Catal., vol. 345, No. 1&2, pp. 67-77 (2003).
Fahrenholtz et al., "Cycloprop[16 α, 17α] androstanes", J. Med. Chem., vol. 15, No. 10, pp. 1056-1060 (1972).
Faia et al., "Depilation induced anagen as a model to study hedgehog pathway antagonist IPI-926: Implications for biomarker development", AACR Meeting Abstracts Online, Abstract #2827, with Infinity Pharmaceuticals Poster, 3 pages (2008).
Fan et al., "Hedgehog signaling promotes prostate xenograft tumor growth", Endocrinology, vol. 145, No. 8, pp. 3961-3970 (2004).
Feldmann et al., "Blockade of hedgehog signaling inhibits pancreatic cancer invasion and metastases: A new paradigm for combination therapy in solid cancers", Cancer Res., vol. 67, No. 5, pp. 2187-2196 (2007).
Feldmann et al., "An orally bioavailable small-molecule inhibitor of Hedgehog signaling inhibits tumor initiation and metastasis in pancreatic cancer", Mol. Cancer Ther., vol. 7, No. 9, pp. 2725-2735 (2008).
Geng et al., "Hedgehog signaling in the murine melanoma microenvironment", Angiogenesis, vol. 10, No. 4, pp. 259-267, DOI: 10.1007/s10456-007-9078-9 (2007).
Genov and Ager, "Asymmetric hydrogenation of ketones catalyzed by $Ru^{II}$-bicp complexes", Angew. Chem. Int. Ed. Engl., vol. 43, No. 21, pp. 2816-2819 (2004).
Giannis et al., "Synthesis of cyclopamine using a biomimetic and diastereoselective approach", Angew. Chem. Int. Ed., vol. 48, pp. 1-5 (2009).
Goldberg et al., "Resolution of odontogenic keratocysts of the jaw in basal cell nevus syndrome with GDC-0449", Arch Dematol., vol. 147, No. 7, pp. 839-841 (2011).
Green, "A new approach to the formal classification of covalent compounds of the elements", Journal of Organometallic Chemistry, vol. 500, Issue 1-2, pp. 127-148 (1995).
Grogan et al., "Synthesis and structure activity relationship of D-homo cyclopamine analogs: A-ring fused heterocyclic analogs", MEDI 97, $237^{th}$ ACS National Meeting, Infinity Pharmaceuticals, Inc., Presenation Poster, with Presentation Abstract, 2 pgs. (2009).
Growdon et al., "Hedgehog pathway inhibitor cyclopamine suppresses Gli1 expression and inhibits serious ovarian cancer xenograft growth", 40th Annual Meeting on Women's Cancer, Feb. 5-8, 2009, Presentation Slides, 16 pages (2009).
"Guidance for industry: Clinical trial endpoints for the approval of cancer drugs and biologics", US Dept. of Health Services, FDA, CDER and CBER, Section III, p. 4-9 (2007).
Guijarro et al., "Achiral β-amino alcohols as efficient ligands for the ruthenium-catalysed asymmetric transfer hydrogenation of sulfinylimines", Tetrahedron Letters, vol. 52, Issue 7, pp. 789-791 (2011), pre-publication accepted manuscript, DOI:10.1016/j.tetlet.2010.12.031, 6 pgs. (2010).
Hanahan et al., "Less is more, regularly: metronomic dosing of cytotoxic drugs can target tumor angiogenesis in mice", J. Clin. Inv., vol. 105, No. 8, pp. 1045-1047 (2000).
Harrington et al., "Targeted radiosensitisation by pegylated liposome-encapsulated 3', 5'-O-dipalmitoyl 5-iodo-2'-deoxyuridine in a head and neck cancer xenograft model," Br. J. Cancer, vol. 91, No. 2, pp. 366-373 (2004).
Harris et al., "Hedgehog signaling: Networking to nurture a premalignant tumor microenvironment", Mol. Cancer Res., vol. 9, No. 9, pp. 1165-1174 (2011).
Hashiguchi et al., "Asymmetric transfer hydrogenation of aromatic ketones catalyzed by chiral ruthenium (II) complexes", J. Am. Chem. Soc., vol. 117, No. 28, pp. 7562-7563 (1995).
Hawley's Condensed Chemical Dictionary, $15^{th}$ edition, Lewis, ed., John Wiley & Sons, New York, pp. 38 and 100 (2007).
Heftmann, "Recent progress in the biochemistry of plant steroids other than steroids (saponins, glycoalkaloids, pregnane derivatives, cardiac glycosides, and sex hormones)", Lipids, vol. 9, No. 8, pp. 626-639 (1974).
Hegde et al., "Hedgehog-induced survival of B-cell chronic lymphocytic leukemia cells in a stromal environment: a potential new therapeutic target", Mol. Cancer Res., vol. 6, No. 12, pp. 1928-1936 (2008).
Heretsch et al., "Cyclopamine and hedgehog signaling: chemistry, biology, medical perspectives", Angew. Chem. Int. Ed., vol. 49, pp. 2-12, DOI: 10.1002/anie.200906967 (2010).
Holton and Necoechea, "Steroids. CLXXV. Further steroidal anabolic agents", J. Med. Chem., pp. 1352-1357 (1962).
Huangfu et al., "Hedgehog signalling in the mouse requires intraflagellar transport proteins", Nature, vol. 426, No. 6962, pp. 83-87 (2003).
Ikariya et al., "Bifunctional transition metal-based molecular catalysts for asymmetric synthesis", Org. Biomol. Chem., vol. 4, No. 3, pp. 393-406 (2006).
Incardona et al., "Cyclopamine inhibition of sonic hedgehog signal transduction is not mediated through effects on cholesterol transport", Dev. Biol., vol. 224, No. 2, pp. 440-452 (2000).
International Search Report from International Patent Application No. PCT/US2005/030406, 2 pages, mailed Apr. 4, 2006, application now published as International Patent Publication No. WO2006/026430 on Mar. 9, 2006.
International Search Report from International Patent Application No. PCT/US2006/010796, 9 pages, mailed May 15, 2008.
International Search Report from International Patent Application No. PCT/US2007/088990, 2 pages, mailed Aug. 1, 2008.
International Search Report from International Patent Application No. PCT/US2007/088995, 6 pages, mailed Aug. 1, 2008.
International Search Report from International Patent Application No. PCT/US2008/003200, 3 pages, mailed Aug. 11, 2008.
International Search Report from International Patent Application No. PCT/US2008/050970, 3 pages, mailed Aug. 22, 2008.
International Search Report from International Patent Application No. PCT/US2008/056229, 4 pages, mailed Aug. 11, 2008.
International Search Report from International Patent Application No. PCT/US2008/088222, 6 pages, mailed Feb. 23, 2009.
International Search Report from International Patent Application No. PCT/US2008/088302, 1 pages, mailed Mar. 25, 2009.
International Search Report from International Patent Application No. PCT/US2009/049372, 3 pages, mailed Mar. 16, 2010.
International Search Report from International Patent Application No. PCT/US2010/021816, 3 pages, mailed Jun. 2, 2010.
International Search Report from International Patent Application No. PCT/US2010/044597, 2 pages, mailed Oct. 1, 2010.
International Search Report from International Patent Application No. PCT/US2010/055879, 12 pages, mailed Jan. 24, 2011.
International Search Report from International Patent Application No. PCT/US2010/057534, 2 pages, mailed Jan. 18, 2011.
International Search Report from International Patent Application No. PCT/US2011/043446, 5 pages, mailed Oct. 16, 2012.
International Search Report from International Patent Application No. PCT/US2011/043453, 4 pages, mailed Mar. 14, 2012.
International Search Report from International Patent Application No. PCT/US2011/051553, 2 pages, mailed Feb. 2, 2012.

(56) References Cited

OTHER PUBLICATIONS

Iselin et al., "Structure of jervine, VI. The sulfuric acid-catalyzed acetolysis of N-acetyl-3-deoxy-3 alpha.-chlorotetrahydrojervine", J. Am. Chem. Soc., vol. 76, pp. 5616-5620 (1954) Database Accession No. 1955:73589, XP-002672119, 4 pgs. (1954).

Iselin et al., "Jervine, IX. Miscellaneous new derivatives", J. Am. Chem. Soc., vol. 78, No. 2, pp. 403-407 (1956) Database Accession No. 1956:69487, XP-002672116. 3 pgs. (1956).

Jacobs and Craig, "The veratrine alkaloids, XXII. On pseudojervine and veratrosine, a companion glycoside in veratrum viride", J. Biol. Chem., vol. 155, 565-572 (1944).

Jacobs and Craig, "The veratrine alkaloids, XXV. The alkaloids of veratrum viride", J. Biol. Chem., vol. 160, pp. 555-565 (1945).

Jacobs and Huebner, "Veratrine alkaloids, XXVII. Further studies with jervine", J. Biol. Chem., vol. 170, pp. 635-652 (1947).

James et al., "Biomedical applications of poisonous plant research", J. Agric. Food Chem., vol. 52, pp. 3211-3230 (2004).

Ji et al., "Protein kinase A, not EPAC, suppresses hedgehog activity and regulates glucocorticoid sensitivity in acute lymphoblastic leukemia cells", J, Biol. Chem., vol. 282, No. 52, pp. 37370-37377 (2007).

Kaneko et al., "Biosynthesis of C-nor-D-homo-steroidal alkaloids from acetate-I-$^{14}$C, cholesterol-4-$^{14}$C and cholesterol-26-$^{14}$C in veratrum grandiflorum", Phytochemistry, vol. 9, pp. 2489-2495 (1970).

Kaneko et al., "11-deoxojervine as a precursor for jervine biosynthesis in veratrum grandiflorum", Phytochemistry, vol. 9, pp. 2497-2501 (1970).

Kaneko et al., "Conversion of solanidine to jervatrum alkaloids in veratrum grandiflorum", Phytochemistry, vol. 11, pp. 3199-3202 (1972).

Kaneko et al., "Biosynthesis of rubijervine in veratrum grandiflorum" Phytochemistry, vol. 14, pp. 1295-1301 (1975).

Kaneko et al., "Origin of nitrogen in the biosynthesis of solanidine by veratrum grandiflorum", Phytochemistry, vol. 15, pp. 1391-1393 (1976).

Kaneko et al., "Dormantinol, a possible precursor in solanidine biosynthesis from budding veratrum grandiflorum" Phytochemistry, vol. 16, pp. 1247-1251 (1977).

Karhadker et al., "Hedgehog signalling in prostate regeneration, neoplasia and metastasis", Nature, 431, pp. 707-712 (2004).

Kayed et al., "Distribution of indian hedgehog and its receptors patched and smoothened in human chronic pancreatitis", J. Endocrinol, vol. 178, No. 3, pp. 467-478 (2003).

Kayed et al., "Indian hedgehog signaling pathway: expression and regulation in pancreatic cancer", Int. J. Cancer; vol. 110, No. 5, pp. 668-676 (2004).

Keeler and Binns, "Chemical compounds of veratrum californicum related to congenital ovine cyclopian malformations: extraction of active material", Proc. Soc. Exptl. Biol. Med., vol. 116, pp. 123-127 (1964).

Keeler and Binns, "Teratogenic compounds of veratrum californicum (Durand), I. Preparation and characterization of fractions and alkaloids for biologic testing", Canadian Journal of Biochemistry, vol. 44, No. 6, pp. 819-828 (1966).

Keeler and Binns, "Teratogenic compounds of veratrum californicum (Durand), II. Production of ovine fetal cyclopia by fractions and alkaloid preparations", Can. J. Biochem., vol. 44, pp. 829-838 (1966).

Keeler, "Teratogenic compounds of veratrum californicum (Durand), IV. First isolation of veratramine and alkaloid Q and a reliable method for isolation of cyclopamine", Phytochemistry, vol. 7, pp. 303-306 (1968).

Keeler, "Toxic and teratogenic alkaloids of western range plants", J. Agr. Food Chem., vol. 17, No. 3, pp. 473-482 (1969).

Keeler, "Teratogenic Compounds of Veratrum Californicum (Durand) VII. The Structure of the glycosidic alkaloid cycloposine", Steroids, vol. 13, No. 5, pp. 579-588 (1969).

Keeler and Binns, "Teratogenic compounds of veratrum californicum as a function of plant part, stage, and site of growth", Phytochemistry, vol. 10, No. 5, pp. 1765-1769 (1971).

Keeler, "Isolation of rubijervine from veratrum-californicum", Phytochemistry, vol. 13, pp. 2336-2337 (1974).

Keeler and Baker, "Oral, osmotic minipump, and intramuscular administration to sheep of the veratrum alkaloid cyclopamine (42970)", Cyclopamine Administration to Sheep, P.S.E.B.M., vol. 192, pp. 153-156 (1989).

Kenney et al., "Hedgehog and PI-3 kinase signaling converge on Nmyc1 to promote cell cycle progression in cerebellar neuronal precursors", Development, vol. 131, No. 1, pp. 217-228 (2004).

Kerbel and Kamen, "The anti-angiogenic basis of metronomic chemotherapy", Nature Rev., Cancer, vol. 4, pp. 423-436 (2004).

King, "Roughening up smoothened: chemical modulators of hedgehog signaling", J. Biol., vol. 1, No. 8, pp. 8.1-8.4 (2002).

Kitajima et al., "Steroid alkaloids of fresh bulbs of fritillaria thunbergii miq. and of crude drug "BAI-MO" prepared therefrom", Heterocycles, vol. 15, No. 2, pp. 791-796 (1981).

Koszelewski et al., "Formal asymmetric biocatalytic reductive animation", Angew. Chem. Int. Ed., vol. 47, No. 48, pp. 9337-9340 (2008).

Koszelewski et al., "ω-transaminases for the synthesis of non-racemic α-chiral primary amines", Trends Biotechnol., vol. 28, No. 6, pp. 324-332 (2010).

Kubo et al., "Hedgehog signaling pathway is a new therapeutic target for patients with breast cancer", Cancer Research, vol. 64, pp. 6071-6074 (2004).

Lacasse et al., "Iodomethylzinc phosphates: powerful reagents for the cyclopropanation of alkenes", J. Am. Chem. Soc., vol. 127, No. 36, pp. 12440-12441 (2005).

Lee et al., "Development of an enzyme-linked immunosorbent assay for the veratrum plant teratogens: cyclopamine and jervine", J. Agric. Food Chem., vol. 51, No. 3, pp. 582-586 (2003).

Leontjev et al., "Reduction of steroidal ketones with amine-boranes", Russian Chemical Bulletin, vol. 53, No. 3, pp. 703-708 (2004).

Lescarbeau et al., "Synthesis and structure activity relationship of D-homo cyclopamine hedgehog antagonists: 7-membered A-ring lactam analogs", MEDI 98, 237th ACS National Meeting, Infinity Pharmaceuticals, Inc., Poster, with Presentation Abstract, 2 pgs. (2009)

Lewis and Veltmaat, "Next stop, the twilight zone: hedgehog network regulation of mammary gland development", J. Mamm. Gland Biol. Neopl., vol. 9, No. 2, pp. 165-181 (2004).

Li et al., "Chemistry, bioactivity and geographical diversity of steroidal alkaloids from the Liliaceae family", Natural Product Reports, vol. 23, pp. 735-752 (2006).

Li et al., "Mesodermal deletion of transforming growth factor-β receptor II disrupts lung epithelial morphogenesis: cross-talk between TGF-β and sonic hedgehog pathways", J. Biol. Chem., vol. 283, No. 52, pp. 36257-36264 (2008).

Lin et al., "Self-renewal of acute lymphomatic leukemia cells is limited by the hedgehog pathway inhibitors cyclopamine and IPI-926", PLoS One, vol. 5, Issue 12, No. e15262, pp. 1-8 (2010).

Lindemann, "Stroma-initiated hedghog signaling takes center stage in B-cell lymphoma", Cancer Res., vol. 68, No. 4, pp. 961-964 (2008).

Lipinski et al., "Dose- and route-dependent teratogenicity, toxicity, and pharmacokinetic profiles of the hedgehog signalling antagonist cyclopamine in the mouse", Toxicol. Sci. Advanced Access Publication, 28 pages, (2008).

Ma et al., "Frequent activation of the hedgehog pathway in advanced gastric adenocarcinomas", Carcinogenesis, vol. 26, No. 10, pp. 1698-1705 (2005).

Ma et al., "Study of sonic hedgehog signaling pathway related molecules in gastric carcinoma", World J. Gastroenterol., vol. 12, No. 25, pp. 2965-3969 (2006).

Ma et al., "Development of in vitro techniques for the important medicinal plant veratrum californicum", Planta Medica, vol. 72, pp. 1142-1148 (2006).

Mandley et al., "The Hh inhibitor IPI-926 delays tumor re-growth of a non-small cell lung cancer xenograft model following treatment

(56) References Cited

OTHER PUBLICATIONS with an EGFR targeted tyrosine kinase inhibitor", Infinity Pharmaceuticals, Inc., Presentation Poster, Abstract #5045, 1 page (2010).
Manna et al., "Metabolite identification of IPI-609, a novel and potent inhibitor of the hedgehog pahway, in different species", Infinity Pharmaceuticals, Inc., Presentation Poster, 1 page (2008).
Mao et al., "First example of asymmetric transfer hydrogenation in water induced by a chiral amino alcohol hydrochloride", Tetrahedron Letters, vol. 46, pp. 7341-7344 (2005).
Masamune et al., "11-Deoxojervine, a new alkaloid form veratrum species", Bull. Chem. Soc. Japan, vol. 38, No. 8, pp. 1374-1378 (1965).
Masamune et al., "Syntheses and NMR spectra of 22,27-imino-17,23-oxidojervane derivatives", Tetrahedron, vol. 23, No. 4, pp. 1591-1612 (1967).
Masamune et al., "Syntheses of jervine and related alkaloids", J, Am. Chem. Soc., vol. 89, No. 17, pp. 4521-4523 (1967).
Masamune et al., "The stereochemistry of dihydrojervine and related compounds: The ORD curves of 11-oxoetiojervanes and 11-oxoiminojervanes", Tetrahedron, vol. 25, Issue 19, pp. 4853-4871 (1969).
Mazur, "Azasteroids III. 3-aza-a-homo androgens", J. Org. Chem., vol. 28, pp. 248-250 (1963).
Meloni et al., "Smoothened signal transduction is promoted by G protein-coupled receptor kinase 2", Mol. Cell. Biol., vol. 26, No. 20, pp. 7550-7560 (2006).
Metcalfe and De Sauvage, "Hedgehog fights back: mechanisms of acquired resistance against smoothened antagonists", Cancer Res; vol. 71, No. 15, pp. 5057-5061 and 6087 (2011).
Mrozik et al., "Heterocyclic steroids in the antiinflammatory series", J. Med. Chem., vol. 7, pp. 584-589 (1964).
Müller-Röver et al., A comprehensive guide for the accurate classification of murine hair follicles in distinct hair cycle stages, J. Invest. Dermatol., vol. 117, No. 1, pp. 3-15 (2001).
Nakamura et al., "Induction of osteogenic differentiation by hedgehog proteins", Biochem. Biophys. Res. Comm., vol. 237, pp. 465-469 Article No. RC977156 (1997).
Niemann et al., "Indian hedgehog and β-catenin signaling: Role in the sebaceous lineage of normal and neoplastic mammalian epidermis". PNAS, vol. 100, Suppl. 1, pp. 11873-11880 (2003).
Nolan-Stevaux et al., "GLI1 is regulated through smoothened-independent mechanisms in neoplastic pancreatic ducts and mediates PDAC cell survival and transformation", Genes Dev., vol. 23, No. 1, pp. 24-36 (2009).
Oatis et al , "Isolation, purification and full NMR assignments to cyclopamine from veratrum californicum", Chemistry Central Journal, vol. 2, No. 12, 17 pgs. (2008).
Ohta et al., "Investigations on steroids. XI. Synthesis of steroidal oxazole, imidazole, and triazole", Chem. Pharm. Bull. vol. 16, No. 8, pp. 1487-1497 (1968).
Ohta et al., "p53-independent negative regulation of p21/cyclin-dependent kinase-interacting protein 1 by the sonic hedgehog-glioma-associated oncogene 1 pathway in gastric carcinoma Cells", Cancer Res., vol. 65, No. 23, pp. 10822-10829 (2005).
Oka and Hara, "Regiospecific Beckmann rearrangement of 3-oxo-4-ene steroid oximes", J. Org. Chem., vol. 43, No. 19, pp. 3790-3791 (1978).
Oka and Hara, "Synthesis of A-azasteroids by the use of specific Beckmann rearrangement", Chemistry and Industry, pp. 168-170 (1969).
Olive et al., "Inhibition of hedgehog signaling enhances delivery of chemotherapy in a mouse model of pancreatic cancer", Science, vol. 324, No. 5933, pp. 1457-1461 (2009).
Oro and Higgins, "Hair cycle regulation of hedgehog signal reception", Dev. Biol., vol. 255, No. 2, pp. 238-248 (2003).
Paladini et al., "Modulation of hair growth with small molecule agonists of the hedgehog signaling pathway", J. Invest. Dermatol., vol. 125, No. 4, pp. 638-646 (2005).

Pan et al., "Discovery of NVP-LDE225, a potent and selective smoothened antagonist", ACS Med. Chem. Lett., vol. 1, No. 3, pp. 130-134 (2010).
Park and Park, "Differential expression of Runx2 and indian hedgehog in cartilaginous tumors", Pathol. Oncol. Res., vol. 13, No. 1, pp. 32-37 (2007).
Paryzek et al., "Ammonium formate/palladium on carbon: A versatile system for catalytic hydrogen transfer reductions of carbon—carbon double bonds", Synthesis, No. 13, pp. 2023-2026 (2003).
Park et al., "A crucial requirement for hedgehog signaling in small cell lung cancer", Nature Med., Author manuscript, vol. 17, No. 11, pp. 1504-1508, DOI: 10.1038/nm.2473 (2012).
Patil et al., "Hedgehog signaling in human hepatocellular carcinoma", Cancer Biol. Ther., vol. 5, No. 1, pp. 111-117 (2006).
Peacock et al., "Hedgehog signaling maintains a tumor stem cell compartment in multiple myeloma", PNAS USA, vol. 104, No. 10, pp. 4048-4053 (2007).
Peacock et al., "Visualization of SMOOTHENED activation supports an essential role for hedgehog signaling in the regulation of self-renewal in small cell lung cancer", Infinity Pharmaceuticals, Inc., 1 page (2009).
Penova and Trandafiloff, "Intensification of extraction processes with tensides", Pharmazie, vol. 26, No. 8, pp. 489-490 (1971) With English Translation.
Philips et al., "Hedgehog signaling antagonist promotes regression of both liver fibrosis and hepatocellular carcinoma in a murine model of primary liver cancer", PLoS One, vol. 6, Issue 9, No. e23943, pp. 1-12 (2011).
Pietsch et al., "Medulloblastomas of the desmoplastic variant carry mutations of the human homologue of *Drosophila* patched", Cancer Research, vol. 57, pp. 2085-2088 (1997).
Pink et al., "Activity of IPI-926, a potent HH pathway inhibitor, in a novel model of medulloblastoma derived from Ptch/HIC +/− mice", Infinity Pharmaceuticals, Inc., AACR Meeting Abstracts Online, 99th AACR Annual Meeting, Apr. 13, 2008; San Diego, CA, Abstract #1588, Presentation Slides, 15 pages (2008).
Proctor et al., "Hedgehog signaling in castration resistant prostate cancer", AACR Annual Meeting, Apr. 17-21, 2010, Infinity Pharmaceuticals, Inc., Abstract #3857, Presentation Slides, 14 pages (2010).
Qualthrough et al., "Hedgehog signalling in colorectal tumour cells: induction of apoptosis with cyclopamine treatment" Int. J. Cancer, vol. 110, No. 6, pp. 831-837 (2004).
Quirk et al., "The smoothened gene and hedgehog signal transduction in *Drosophila* and vertebrate development", Cold Spring Harbor Symposium Quant. Biol., vol. 62, pp. 217-226 (1997).
Rahman et al., "Alkaloids from veratrum album", Phytochemistry, vol. 30, No. 1, pp. 368-370 (1991).
Rahman and Choudhary, "Chemistry and biology of steroidal alkaloids", The Alkaloids, Cordell, ed., Academic Press, San Diego, vol. 50, Ch. 2, pp. 61-108 (1998).
Rasmusson et al., "Azasteroids: structure-activity relationships for inhibition of 5α-reductase and of androgen receptor binding", J. Med. Chem., vol. 29, pp. 2298-2315 (1986).
Ravasio and Rossi, "Selective hydrogenations promoted by copper catalysts. 1. Chemoselectivity, regioselectivity, and stereoselectivity in the hydrogenation of 3-substituted steroids", J. Org. Chem., vol. 56, No. 13, pp. 4329-4333 (1991).
Read, "Direct targeting of tumor cells with smoothed inhibitor IPI-926", 2011 AACR Read IPI-926 Direct Targeting, Infinity Pharmaceuticals, Inc., Presentation Slides, 27 pages (2011).
Reddy et al., "A new novel and practical one pot methodology for conversion of alcohols to amines", Synthetic Communications, vol. 30, No. 12, pp. 2233-2237 (2000).
Reetz and Li, "An efficient catalyst system for the asymmetric transfer hydrogenation of ketones: remarkably broad substrate scope", J. Am. Chem. Soc., vol. 128, No. 4, pp. 1044-1045 (2006).
Reifenberger et al., "Missense mutations in SMOH in sporadic basal cell carcinomas of the skin and primitive neuroectodermal tumors of the central nervous system", Cancer Research, vol. 58, pp. 1798-1803 (1998).
Remingtons Pharmaceutical Sciences, 17$^{th}$ Edition, Gennaro, ed., Mack Publishing Company, Easton, Pennsylvania 18042, p. 1625 (1985).

(56) References Cited

OTHER PUBLICATIONS

Rohatgi et al., "Patched1 regulares hedgehog signaling at the primary cilium", Science, vol. 317, No. 5836, pp. 372-376 (2007).
Rominger et al., "Evidence for allosteric interactions of antagonist binding to the smoothened receptor", J. Pharmacol. Exp. Ther., vol. 329, No. 3, pp. 995-1005 (2009).
Ross, "A Study Evaluating IPI-926 in combination with gemcitabine in patients with metastatic pancreatic cancer", National Cancer Institute, Clinical Trials (PDQ®), Data processed on Oct. 17, 2013, 3 pgs., Retreived from the internet http://www.cancer.gov/clinicaltrials/search/view?cdrid=674592&version=HealthProfessional.
Rubin and De Sauvage, "Targeting the hedgehog pathway in cancer", Nature Rev., vol. 5, No. 12, pp. 1026-1033 (2006).
Rudin et al., "Treatment of medulloblastoma with hedgehog pathway inhibitor GDC-0449", N. Eng. J. Med., vol. 361, No. 12, pp. 1173-1178 (2009).
Rudin et al., "A phase 1 study of IPI-926, an inhibitor of the hedgehog pathway, in patients with advanced or metastatic solid tumors", Infinity Pharmaceuticals, Inc., Poster, 1 page. (2010).
Saldanha, "The hedgehog signalling pathway and cancer", J. Pathol., vol. 193, No. 4, pp. 427-432 (2001).
Sanganwar and Gupta, "Dissolution-rate enhancement of fenofibrate by adsorption onto silica using supercritical carbon dioxide", Int. J. Pharm., vol. 360, No. 1-2, pp. 213-218 (2008).
Sasson et al., "Homogeneous catalytic transfer-hydrogenation of a, β-unsaturated carbonyl compounds by dichlorotris (triphenylphosphine) ruthenium (II)", Tetrahedron Letters, vol. 12, Issue. 24, pp. 2167-2170 (1971).
Sato et al., "Induction of the hair growth phase in postnatal mice by localized transient expression of Sonic hedgehog", J. Clin. Invest., vol. 104, No. 7, pp. 855-864 (1999).
Sato et al., "Effect of adenovirus-mediated expression of sonic hedgehog gene on hair regrowth in mice with chemotherapy-induced alopecia", J. Natl. Cancer Inst., vol. 93, No. 24, pp. 1858-1864 (2001).
Sawada et al., "Asymmetric catalysis of intramolecular cyclopropanation of 5-aryl-1-diazo-1-mesitylsulfonyl-5-hexen-2-ones", Adv. Synth. Catal., vol. 347, Issue 11-13, pp. 1527-1532 (2005).
Shafaee et al., "Cyclopamine increases the cytotoxic effects of paclitaxel and radiation but not cisplatin and gemcitabine in hedgehog expressing pancreatic cancer cells", Cancer Chemother. Pharmacol., vol. 58, No. 6, pp. 765-770 (2006), Original Article, 6 pgs., DOI:10.1007/s00280-006-0227-4 (2006).
Shafiee et al., "Enzymatic deglycosylation of enfumafungin, a triterpene glycoside natural product, and its chemically synthesized analogues", J. Mol. Catalysis B: Enzymatic, vol. 16, pp. 27-32 (2001).
Shaw et al., "The sonic hedgehog pathway stimulates prostate tumor growth by paracrine signaling and recapitulates embryonic gene expression in tumor myofibroblasts", Oncogene, vol. 28, No. 50, pp. 4480-4490 (2009).
Sheng et al., "Activation of the hedgehog pathway in advanced prostate cancer", Molecular Cancer, vol. 3, No. 29, 13 pages (2004).
Sheng et al., "Regulation of Gli1 localization by the cAMP/protein kinase A signaling axis through a site near the nuclear localization signal", J. Biol. Chem. vol. 281, No. 1, pp. 9-12 (2006).
Shibasaki et al., "Hydrolysis of conjugated steroids by the combined use of β-glucuronidase preparations from Helix pomatia and Ampullaria: Determination of urinary cortisol and its metabolites", Steroids, vol. 66, pp. 795-801 (2001).
Shin et al., "Hedgehog / WNT feedback supports regenerative proliferation of epithelial stem cells in bladder", Nature, vol. 472, No. 7341, pp. 110-114, Author Manuscript, 15 pgs. (2011).
Shiotani et al., "Sonic hedgehog and CDX2 expression in the stomach", J. Gastroenterol. Hepatol., vol. 23, Suppl. 2, pp. S161-S166 (2008).
Shner et al., "The sterospecificity of the hydrogenation of 16α-methyl-3-oxo-$\Delta^4$-unsaturated compounds", Chemistry of Natural Compounds, vol. 6, No. 1, pp. 48-51 (1970).
Shroff and Harper, "3-Aza-A-homoandrostenes" J. Med. Chem., vol. 12, No. 1, pp. 190-191 (1969).
Sicklick et al., "Hedgehog signaling correlates with heptacellular carcinoma progression" J. Clinical Oncology, 2005 ASCO Annual Meeting Proceedings, vol. 23, No. 16s (Jun. 1 Supplement), Abstract #9610, 1 page (2005).
Sicklick et al., "Hedgehog signaling maintains resident hepatic progenitors throughout life", Am. J. Physiol. Gastrointenst. Liver Physiol., vol. 290, No. 5, pp. G589-G670 (2006).
Sicklick et al., "Dysregulation of the hedgehog pathway in human hepatocarcinogenesis", Carcinogenesis, vol. 27, No. 4, pp. 748-757 (2006).
Sims-Mourtada et al., "Hedgehog: an attribute to tumor regrowth after chemoradiotherapy and a target to improve radiation response", Clin. Cancer Res., vol. 12, No. 21, pp. 6565-6572 (2006).
Singh et al., "Hedgehog-producing cancer cells respond to and require autocrine hedgehog activity", Cancer Res.; vol. 71, No. 13, pp. 4454-4463 (2011).
Siu et al., "A first-in-human, phase I study of an oral hedgehog (HH) pathway antagonist, BMS-833923 (XL 139), in subjects with advanced or metastatic solid tumors", J. Clin Oncol., vol. 28, pp. 15s, Suppl. Abstract#2501, 3 pgs.(2010) Abstract Only.
Skipper et al., "In vivo efficacy of marimastat and chemoradiation in head and neck cancer xenografts", ORL, vol. 71, No. 1, pp. 1-5, Original Paper, DOI:10.1159/000163217 (2009).
Skvara et al., "Topical treatment of basal cell carcinomas in nevoid basal cell carcinoma syndrome with a smoothened inhibitor", J. Invest. Dermatol., vol. 131, No. 8, pp. 1735-1744 Original Article, DOI:10.1038/jid.2011.48 (2011).
Smith and Thomas, "Animal models for the study of squamos cell carcinoma of the upper aerodigestive tract: a historical perspective with review of their utility and limitations, Part A. Chemically-induced de novo cancer, syngenic animal models of HNSCC, animal models of transplanted xenogenic human tumors," Int. J. Cancer, vol. 118, No. 9, pp. 2111-2122 (2006).
Stanton et al., "Small-molecule modulators of the sonic hedgehog signaling pathway", Mol. Biosyst., vol. 6, pp. 44-54 (2010).
Stecca et al., "Melanomas require HEDGEHOG-GLI signaling regulated by interactions between GLI1 and the RAS-MEK/AKT pathways", PNAS, vol. 104, No. 14, pp. 5895-5900 (2007).
Steg et al., "Multiple gene expression analyses in paraffin-embedded tissues by TaqMan low-density array, application to hedgehog and Wnt pathway analysis in ovarian endometroid adenocarcinoma", J. Mol. Diagn., vol. 8, No. 1, pp. 76-83 (2006).
Suggs et al., "Facile homogeneous hydrogenations of hindered olefins with [Ir(cod)py(PCy$_3$)]PF$_6$", Tetrahedron Letters, vol. 22, Issue 4, pp. 303-306 (1981).
Suginome et al., "Synthesis of O,N-diacetyl-3β-hydroxy-5α,12α-jervan-11-one with 17-epi-configuration by hypoiodite reaction (1,2)", Tetrahedron Letters, vol. 14, No. 42, pp. 4147-4150 (1973).
Suginome et al., "Photo-induced Radical Rearrangements of Hypoiodite of N-Acetyljervine and the Related C-nor-D-Homosteroid in the Presence of Mercury (II) Oxide and Iodine", Bull. Chem. Soc. Japan, vol. 54, No. 10, pp. 3042-3047 (1981).
Suginome et al., "The transformation of Jervine into 18-Functional D-Homo-C-Norsteriods. IV. The Transformation of Jervine into (20R)-18,20-β-epoxy-3β-hydroxy-17β-ethyletiojervan-18-one 3-acetate via (20R)-18,20β-epoxy-3β-hydroxy-12α,17β-ethyletiojervan-11-one 3-acetate", Bull. Chem. Soc. Jpn., vol. 54, No. 3, pp. 852-861 (1981).
Sydor et al., "Activity of IPI-926, a novel inhibitor of the HH pathway, in subcutaneous and orthotopically implanted xenograft tumors that express SHH ligand", Eur. J. Cancer, Supplement, vol. 6, No. 12, p. 179, Poster 570 (2008).
Taipale et al., "Effects of oncogenic mutations on smoothened and patched can be reversed by cyclopamine", Nature, vol. 406, No. 6799, pp. 1005-1009 (2000).
Tannock et al., "Docetaxel plus prednisone or mitoxantrone plus prednisone for advanced prostate cancer", N. Eng. J. Med., vol. 351, No. 15, pp. 1502-1512 (2004).
Tas and Avci, "Rapid clearance of psoriatic skin lesions induced by topical cyclopamine", Dermatology, vol. 209 pp. 126-131 (2004).

(56) References Cited

OTHER PUBLICATIONS

Thayer et al., "Hedgehog is an early and late mediator of pancreatic cancer tumorigenesis", Nature, vol. 425, pp. 851-856 (2003).
Thievessen et al., J. "Hedgehog signaling in normal urothelial cells and urothelial carcinoma cell lines", J. Cell Physiol., vol. 203, No. 2, pp. 372-377 (2005) Abstract Only.
Travaglione et al., "Activity of IPI-926, a novel inhibitor of the Hh pathway, in subcutaneous and orthotopically implanted xenograft tumors that express SHh ligand", Infinity Pharmaceuticals, Inc., Presentation Poster, 1 page (2008).
Travaglione et al., "A novel HH pathway inhibitor, IPI-926, delays recurrence post-chemotherapy in a primary human SCLC xenograft model", AACR Meeting Abstracts Online, $99^{th}$ AACR Annual Meeting, Apr. 12-16, 2008, San Diego, CA, Abstract #4611, 2 pags (2008).
Travaglione et al., "Induction of tumor-derived hedgehog ligand by chemotherapy", Infinity Pharmaceuticals, Inc., Presentation Poster, Abstract #323, 1 page (2009).
Travaglione et al., "The Hh inhibitor IPI-926 enhances tumor perfusion and nab-paclitaxel activity in a pancreatic xenograft model", Infinity Pharmaceuticals, Inc., Presentation Poster, Abstract #LB-374, 1 page (2010).
Tremblay et al., "Synthesis of novel, chemically stable D-homo-cyclopamine analogs via a cyclopropanation/ring-expansion sequence", Infinity Pharmaceuticals, Inc., 1 page (2007).
Tremblay et al., "Semisynthetic cyclopamine analogues as potent and orally bioavailable hedgehog pathway antagonists", J. Med. Chem., vol. 51, No. 21, pp. 6646-6649 (2008).
Tremblay et al., "Synthesis and structure activity relationship of D-homo cyclopamine analogs: 3-substituted analogs", Infinity Pharmaceuticals, Inc., Presentation Poster, 1 page (2009).
Tremblay et al., "Discovery of IPI-926, a semi-synthetic clinical candidate that targets the hedgehog pathway", Infinity Pharmaceuticals, Inc., ACS Meeting Salt Lake City, UT on Mar. 25, 2009, Presentation Slides, 26 pages (2009).
Tremblay et al., "Discovery of a potent and orally active hedgehog pathway antagonist (IPI-926)", J. Med. Chem., vol. 52, No. 14, pp. 4400-4418 (2009).
Tremblay et al., "Recent patents for hedgehog pathway inhibitors for the treatment of malignancy", Expert Opin. Ther. Pat., vol. 19, No. 8, pp. 1039-1056 (2009).
Tremblay et al., "New Developments in the discovery of small molecule Hedgehog pathway antagonists", Curr. Opin. Chem. Biol., vol. 14, No. 3, pp. 428-435 (2010) Article in press, COCHBI-737, vol. 14, pp. 1-8 (2010).
Tremblay et al., "Development of multi-kilogram synthetic route to IPI-926, a novel hedgehog pathway antagonistic for the treatment of malignant diseases", Infinity Pharmaceuticals, Inc., Apr. 2, 2011, Presentation Slides, 29 pages (2011).
Tschesche et al., "Zur biosynthese von steroid-derivaten im pflanzenreich, 3. Mitt.: spirostanol-biogenese aus cholesterin-glucosid", Z. Naturforsch, vol. 21b pp. 494-495 (1966) German Language Only.
Tsuji et al., "Highly stereoselective hydrogenation of 3-oxo4-ene and -1,4-diene steroids to 5β compounds with palladium catalyst", J. Org. Chem., vol. 45, pp. 2729-2731 (1980).
Turner et al., "Sonic hedgehog pathway inhibition alters epididymal function as assessed by the development of sperm motility", Journal of Andrology, vol. 27, No. 2, pp. 225-232 (2006).
Van Der Horst et al., "Hedgehog stimulates only osteoblastic differentiation of undifferentiated KS483 cells", Bone, vol. 33, No. 6, pp. 899-910 (2003).
Vanhook, "Focus issue: fine-tuning hedgehog signaling in development and disease", Sci. Signaling, vol. 4, Issue 200, No. eg10, pp. 1-2 (2011).
Van Weerden et al., "Human xenograft models as useful tools to assess the potential of novel therapeutics in prostate cancer", Br. J. Cancer, vol. 100, No. 1, pp. 13-18 (2009).
Veratrum nigrum, Wikipedia entry last updated Apr. 23, 2014, Retreived from the internet http://en.wikipedia.org/wiki/Veratrum_nigram.

Villavicencio et al., "The sonic hedgehog-patched-gli pathway in human development and disease", Am. J. Hum. Genet., vol. 67, No. 5, pp. 1047-1054 (2000).
Villavicencio et al., "Activity of the Hh pathway inhibitor IPI-926 in a mouse model of medullablastoma", Infinity Pharmaceuticals, Inc., Abstract #3199, Presentation Poster, 1 page (2009).
Voituriez and Charette, "Enantioselective cyclopropanation with TADDOL-derived phosphate ligands", Adv. Synth. Catal., vol. 348, Issue 16-17, pp. 2363-2370 (2006).
Von Hoff et al., "Inhibition of the hedgehog pathway in advanced basal-cell carcinoma", N. Eng. J. Med., vol. 361, No. 12, pp. 1164-1172 (2009).
Wang et al., "Revision of structure of peimisine", Yao Xue Xue Bao, vol. 27, No. 4, pp. 273-278 (1992) Database Accession No. 1992:490583, (1992).
Wanshura et al., "Sequential activation of snail1 and N-Myc modulates sonic hedgehog-induced transformation of neural cells", Cancer Res.; vol. 71, No. 15, pp. 5336-5345 (2011).
Warzecha et al., "Inhibition of osteosarcoma cell proliferation by the hedgehog-inhibitor cyclopamine", J. Chemother., vol. 19, No. 5, pp. 554-561 (2007).
Watkins et al., "Hedgehog signaling within airway epithelial progenitors and in small-cell lung cancer", Nature, vol. 422, pp. 313-317 (2003).
Wei et al., "Indian hedgehog and its targets in human endometrium: menstrual cycle expression and response to CDB-2914", J. Clin. Endocrinol. Metab., vol. 95, No. 12, pp. 5530-5337 (2010).
Williams et al., "Identification of a small molecule inhibitor of the hedgehog signaling pathway: affects on basal cell carcinoma-like lesions", PNAS USA, vol. 100, No. 8, pp. 4616-4621 (2003).
Wintersteiner et al., "Structure of jervine, V. The sulfuric acid-catalyzed acetolysis of diacetyltetrahydrojervine", J. Am. Chem. Soc., vol. 76, No. 22, pp. 5609-5616 (1954) Database Accession No. 1955:73588 (1954).
Wong et al., "Primary cilia can both mediate and suppress Hedgehog pathway-dependent tumorigenesis", Nat. Med., vol. 15, No. 9, pp. 1055-1061 (2009).
Yu et al., "Chemical constituent of hubeibeimu, V. Isolation and identification of hupehenisine", Yaoxue Xuebao, vol. 21, No. 7, pp. 546-550 (1986) Databse Accession No. 1987:15699 (1987).
Wunder et al., "Opportunities for improving the therapeutic ratio for patients with sarcoma", Lancet Oncol., vol. 8, No. 6, pp. 513-524 (2007).
Xie et al., "Activating smoothened mutations in sporadic basal-cell carcinoma", Nature, vol. 391, pp. 90-92 (1998).
Yang and Hinds, "pRb-mediated control of epithelial cell proliferation and Indian Hedgehog expression in mouse intestinal development", BMC Developmental Biology, vol. 7, No. 6, pp. 1-12 (2007).
Yauch et al., "Smoothened mutation confers resistance to a hedgehog pathway inhibitor in medulloblastoma", Science, vol. 326, No. 5952, pp. 572-574 (2009).
Yoo et al., "Sonic hedgehog signaling promotes motility and invasiveness of gastric cancer cells through TGF-β-mediated activation of the ALK5-smad 3 pathway", Carcinogenesis, vol. 29, No. 3, pp. 480-490 (2008).
Yoshizaki et al., "Expressions of sonic hedgehog, patched, smoothened and Gli-1 in human intestinal stromal tumors and their correlation with prognosis", World J. Gastroenterol., vol. 12, No. 35, pp. 5687-5691 (2006).
Yu et al., "Chemical consituents of the unibract fritillary (*Fritillaria unibracteata*)", Zhongcaoyao, vol. 21, No. 1, pp. 2-6 (1990), Database Accession No. 1990:512481 (1990).
Yukihiko, "Hidorokishiruki yuyou no Simmons-Smith Hannou", Kagaku, vol. 61, No. 1, pp. 63-64 (2006) Japanese Language Only.
Yun et al., "Simultaneous synthesis of enantiomerically pure (R)-1-phenylethanol and (R)-α-methylbenzylamine from racemic α-methylbenzylamine using ω-transaminase/alcohol dehydrogenase/glucose dehydrogenase coupling reaction", Biotechnol. Lett., vol. 25, No. 10, pp. 809-814 (2003).
Yun et al., "ω-Amino acid: Pyruvate transaminase from Alcaligenes denitrificans Y2k-2: A new catalyst for kinetic resolution of β-amino acids and amines", Appl. Environ. Microbiol., vol. 70, No. 4, pp. 2529-2534 (2004).

(56) References Cited

OTHER PUBLICATIONS

Zassoinovich et al., "Asymmetric hydrogen transfer reactions promoted by homogeneous transition metal catalysts", Chem. Rev., vol. 92, No. 5, pp. 1051-1069 (1992).

Zeisberg and Neilson, "Biomarkers for epithelial-mesenchymal transitions", J. Clin. Invest., vol. 119, No. 6, pp. 1429-1437 (2009).

Zeng et al., "Neurosteroid analogues. 10. The effect of methyl group substitution at the C-6 and C-7 positions on the GABA modulatory and anesthetic actions of (3α,5α)- and (3α, 5β)-3-hydroxypregnan-20-one", J. Med. Chem., vol. 48, No. 8, pp. 3051-3059 (2005).

Zhang et al., "Hedgehog pathway responsiveness correlates with the presence of primary cilia on prostate stromal cells", BMC Developmental Biology, vol. 9, No. 50, pp. 1-7 (2009).

Zhao et al., "Studies on the constituents of veratrum plants II. Constituents of *Veratrum nigrum* L. var. *ussuriense* (1). Structure and $^1$H- and $^{13}$C-nuclear magnetic resonance spectra of a new alkaloid, verussurinine, and related alkaloids", Chem. Pharm. Bull., vol. 39, No. 3, 549-554 (1991).

Zhao et al., "Hedgehog signalling is essential for maintenance of cancer stem cells in myeloid leukaemia", Nature, vol. 460, No. 7255, pp. 652-656 (2009) Pre-Publication Article DOI: 10.1038/nature07737, pp. 1-5 (2009).

Alonso et al., "Ru(arene)(amino alcohol)-catalyzed transfer hydrogenation of ketones: mechanism and origin of enantioselectivity", J. Am. Chem. Soc., vol. 121, pp. 9580-9588 (1999).

Dersnah and Baird, "Chiral $\eta^6$-$C_6H_6$ ruthehium complexes", J. Org. Chem., vol. 127, C55-C58 (1977).

Noyori and Hashiguchi, "Asymmetric transfer hydrogenation catalyzed by chiral ruthenium complexes", Acc. Chem. Res., vol. 30, No. 2, pp. 97-102 (1997).

Yamakawa et al., "CH/π attraction: the origin of enantioselectivity in transfer hydrogenation of aromatic carbonyl compounds catalyzed by chiral $\eta^6$-arene-ruthenium(II) complexes", Angew. Chem. Int. Ed., vol. 40, No. 15, pp. 2818-2821 (2001).

METHODS FOR STEREOSELECTIVE REDUCTION

CROSS-REFERENCE TO RELATED APPLICATIONS

This application is a continuation of U.S. patent application Ser. No. 12/810,600, filed Sep. 15, 2010, now U.S. Pat. No. 8,716,479, which is the U.S. National Stage of PCT/US2008/088302, filed Dec. 24, 2008, which is a continuation-in-part of U.S. patent application Ser. No. 11/965,688, filed Dec. 27, 2007, now U.S. Pat. No. 7,812,164, and which claims the benefit of U.S. Provisional Application No. 61/017,162, filed Dec. 27, 2007, each of these prior applications is incorporated by reference in its entirety.

BACKGROUND

Polycyclic compounds such as steroidal compounds have a wide variety of uses, for example, as pharmaceutical agents. In steroidal compounds that contain enone moieties, it is sometimes desirable to stereoselectively reduce the C—C double bond to preferentially produce either the β-reduced or the α-reduced compound. In either event, it is useful to reduce the C—C double bond stereoselectively in order to obviate complex chromatographic purifications.

SUMMARY

The invention relates to a method of reducing the C—C double bond of an enone of a steroidal compound to produce a mixture of β ketone product and α ketone product, by treating a solution or suspension of the steroidal compound in a solvent with hydrogen gas in the presence of a catalyst and a substituted pyridine. In some instances, an excess of the β ketone product is produced compared to the α ketone product. The invention also relates to compounds made by the described methods.

DETAILED DESCRIPTION

In one aspect, the invention relates to a method of reducing the C—C double bond of an enone of a steroidal compound to produce a mixture of β ketone product and a ketone product, the method comprising treating a solution or suspension of the steroidal compound in a solvent with hydrogen gas in the presence of a catalyst and a substituted pyridine. In some embodiments, an excess of the β ketone product is produced compared to the α ketone product. For example, the ratio of the β ketone product to the α ketone product can be at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1.

In some embodiments, the substituted pyridine is a 3-substituted pyridine. Examples of suitable 3-substituted pyridines include 3-picoline, 3-methoxypyridine, 3-ethylpyridine, 3-n-butylpyridine, 3-isobutylpyridine, 3-hydroxypyridine, 3-aminopyridine, and 3-dimethylaminopyridine. In other embodiments, the substituted pyridine is a 4-substituted pyridine (e.g., 4-picoline, 4-methoxypyridine, 4-aminopyridine, or 4-dimethylaminopyridine).

In some embodiments, the substituted pyridine is the reaction solvent. In other embodiments, the solvent is a solvent other than the substituted pyridine. Any solvent that does not interfere with the reduction reaction may be employed, including, for example, ethers (e.g., THF), chlorinated solvents (e.g., chloroform, dichloromethane) and aromatics (e.g., benzene, toluene). In addition, a mixture of one or more solvents may be used. When another solvent is used, the v/v percentage of substituted pyridine to the total volume can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 99%.

Suitable hydrogenation catalysts include heterogeneous catalysts and homogeneous catalysts. Examples of homogeneous catalysts include, for example, metal catalysts based on nickel (e.g., Raney nickel, nickel boride), palladium (e.g., Pd/C), platinum (e.g., platinum oxide), rhodium, ruthenium, or zinc (e.g., zinc oxide). Examples of homogeneous catalysts include, for example, metal catalysts based on rhodium (e.g., Wilkinson's catalyst), ruthenium, palladium, platinum or cobalt. Any hydrogenation catalyst known in the art to reduce the double bond of an enone may be employed (see, e.g., March, *Advanced Organic Chemistry*). In some embodiments, the catalyst is a palladium-based catalyst, for example, palladium on carbon (e.g., 5% or 10% Pd/C), palladium on $Al_2O_3$, palladium hydroxide on carbon (Pearlman's catalyst), and palladium and platinum on carbon (e.g., 4% Pd/1% Pt on carbon). Suitable hydrogenation catalysts can be obtained from commercial sources (e.g., Johnson Matthey).

In some embodiments, the hydrogen is applied to the reaction at or near atmospheric pressure (i.e., at 1 atm.) for example, under balloon pressure. In other embodiments, the hydrogen is applied to the reaction at increased pressure (e.g., 1 to 5 atm. or greater), for example, using a Parr shaker or similar apparatus.

The method of the invention provides for stereoselective hydrogenation of an enone double bond present in a steroidal compound. Steroidal compounds generally contain a fused four-ring system core. For example, steroidal ring systems can include 6, 6, 6, 5 ring systems (e.g., cyclopenta[a]phenanthrene) or 6, 6, 5, 6, ring systems, wherein each ring is designated A, B, C, or D as shown below:

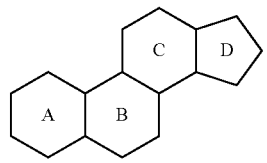

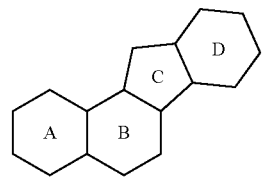

Steroidal compounds also include homo-analogs (i.e., wherein one or more rings contain additional carbons) and nor-analogs (i.e., wherein one or more rings contain one or more fewer carbons), and mixtures of both (i.e., wherein one or more rings contain additional carbons and one or more rings contain fewer carbons). One such example is the 6, 6, 5, 7 ring system:

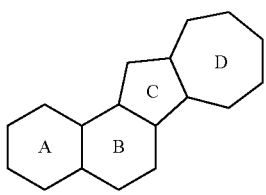

In addition, one or more additional rings may be fused or bonded to the steroidal core. Included within this group are steroidal alkaloids having the following general structures:

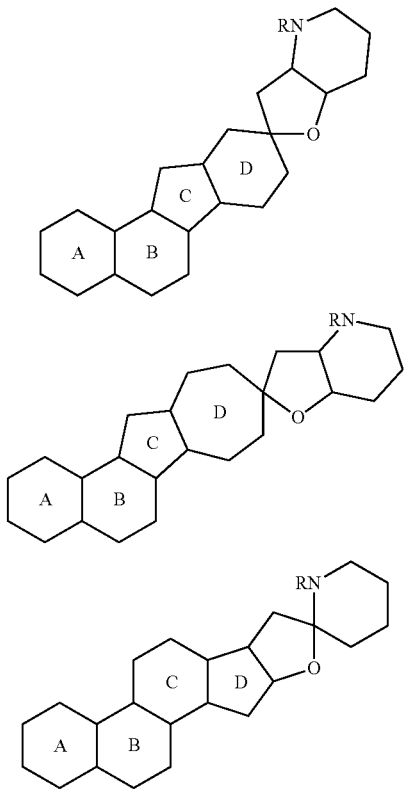

Steroidal compounds also include des-analogs, wherein one of the four fused rings is missing (e.g., a 6, 6, 5 ring system).

Generally, the enone that is reduced according to the present invention is present in the A ring of the steroidal compound. The ketone carbonyl may be bonded to any carbon of the A ring (as valency permits), and one or more double bonds may be present in the ring. For example, the enone may have any of the following configurations:

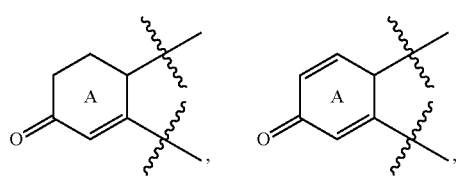

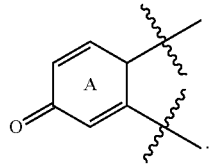

When the rings of a steroid are denoted with the A ring on the left (as shown herein), an atom or group attached to a ring is termed α if it lies below the plane of the paper and β if it lies above the plane of the paper:

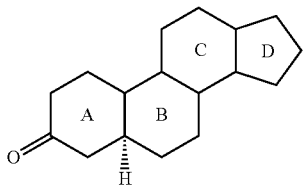

α reduction product

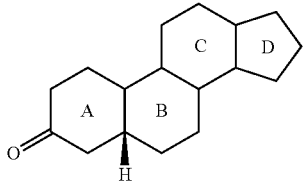

β reduction product

Any of the carbons in the steroidal backbone may bear substituents. Exemplary substituents include hydrogen, optionally substituted alkyl, optionally substituted alkenyl, optionally substituted alkynyl, halogen, hydroxyl, optionally substituted alkoxyl, optionally substituted amino, optionally substituted amido, optionally substituted aryl, optionally substituted heteroaryl, carbonyl, carboxyl, optionally substituted ether, optionally substituted thioether, optionally substituted alkylsulfonyl, optionally substituted arylsulfonyl, optionally substituted ketone, optionally substituted ester, and the like.

Steroidal compounds can be naturally occurring, semi-synthetic, or fully synthetic. The enone moiety can be present in the naturally occurring steroidal compound (e.g., testosterone) or it may be introduced synthetically, e.g., an enone of cyclopamine as shown below:

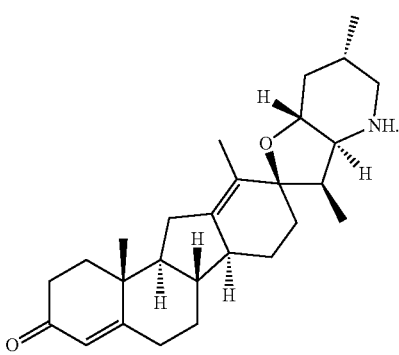

Examples of steroidal compounds that have enone moieties or that can be modified to contain enone moieties include, but are not limited to, cholestanes, cholanes, pregnanes, androstanes, estranges, progestagens, brassinosteroids, bufadienolides, cardenolides, cucurbitacins, ecdysteroids, sapogenins, steroid alkaloids, anabolic steroids, withasteroids, bile acids, hormonal steroids (e.g., sexual hormones, corticosteroids, neurosteroids), glucocorticoids, mineralocorticoids, and the like. Examples include compounds having the following general structures:

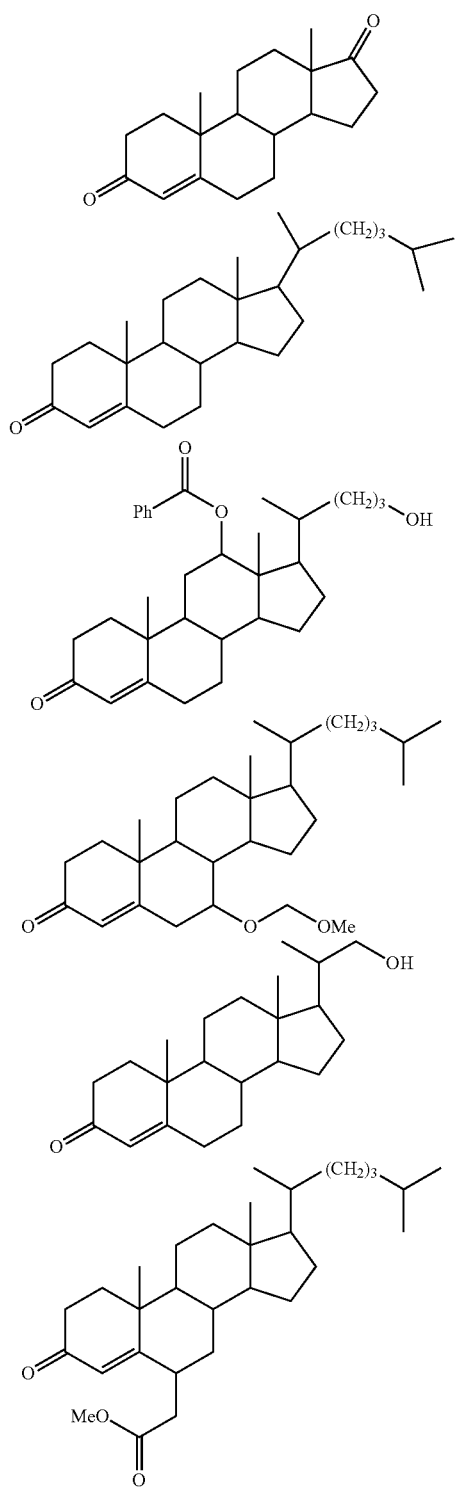

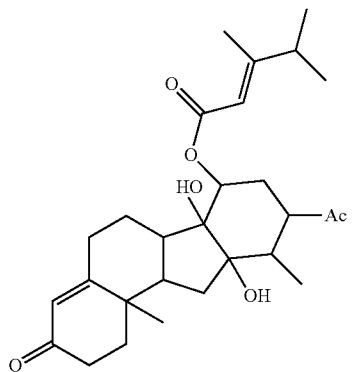

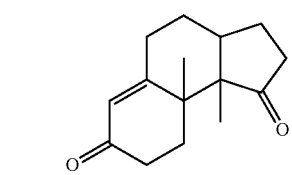

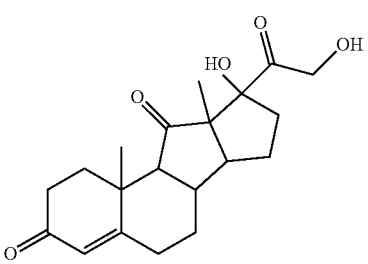

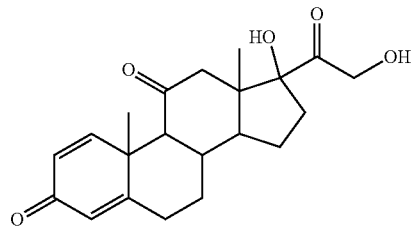

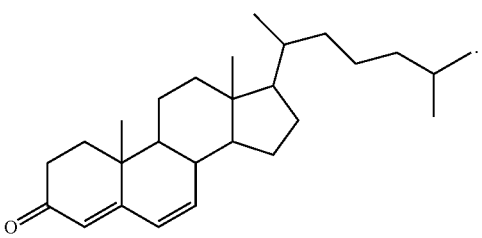

and

Further examples of steroidal compounds that can be reduced according to the present invention include compounds of Formula A:

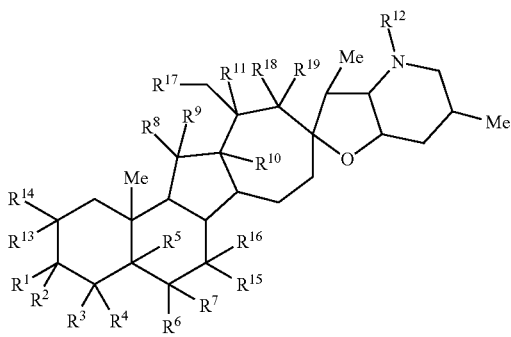

or a pharmaceutically acceptable salt thereof; wherein $R^1$ and $R^2$ taken together with the carbon to which they are bound form a carbonyl;

$R^8$ is H, alkyl, alkenyl, alkynyl, aryl, cycloalkyl, heterocloalkyl, aralkyl, heteroaryl, heteroaralkyl, halide, sulfhydryl, alkylthio, arylthio, aralkylthio, hydroxyl, alkoxyl, aryloxy, acyloxy, amino, alkylamino, arylamino, acylamino, aralkylamino, nitro, acylthio, carboxamide, sulfonamide, carboxyl, nitrile, sulfate, —OP(L)(OR$^{20}$)$_2$, —X—C(L)-R$^{21}$ or —X—C(L)-X—R$^{21}$;

X is O or NR wherein R is H, alkyl, alkenyl, alkynyl, aryl, cycloalkyl or aralkyl;

L is O or S;

$R^9$ is H, alkyl, alkenyl, alkynyl, aryl, cycloalkyl, heterocloalkyl, aralkyl, alkoxyl, aryloxy, acyloxy, halide, sulfhydryl, alkylthio, arylthio, aralkylthio, hydroxyl, amino, alkylamino, arylamino, acylamino, aralkylamino, heteroaryl, or heteroaralkyl;

$R^4$ and $R^5$ taken together form a double bond;

$R^{10}$ and $R^{11}$ taken together form a double bond or form a group represented by 1b

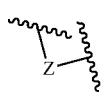

wherein Z is NR$^{21}$, O, or C(R$^{23}$)(R$^{23}$);

$R^{12}$ is H, alkyl, alkenyl, alkynyl, aryl, cycloalkyl, heterocycloalkyl, hydroxyl, aralkyl, heteroaryl, heteroaralkyl, haloalkyl, alkoxyl, —C(O)R$^{21}$, —CO$_2$R$^{21}$, —SO$_2$R$^{21}$, —C(O)N(R$^{21}$)(R$^{21}$), —[C(R$^{21}$)$_2$]$_q$—R$^{21}$, —[(W)—N(R$^{21}$)C(O)]$_q$R$^{21}$, —[(W)—C(O)]$_q$R$^{21}$, —[(W)—C(O)O]$_q$R$^{21}$, —[(W)—OC(O)]$_q$R$^{21}$, —[(W)—SO$_2$]$_q$R$^{21}$, —[(W)—N(R$^{21}$)SO$_2$]$_q$R$^{21}$, —[(W)—C(O)N(R$^{21}$)]$_q$R$^{21}$, —[(W)—O]$_q$R$^{21}$, —[(W)—N(R$^{21}$)]$_q$R$^{21}$, or —[(W)—S]$_q$R$^{21}$;

W is a diradical, and q is 1, 2, 3, 4, 5, or 6;

$R^{15}$, $R^{16}$, and $R^{17}$ are independently H, alkoxyl, aryloxy, acyloxy, halide, hydroxyl, amino, alkylamino, arylamino, acylamino, aralkylamino; or $R^{15}$ and $R^{16}$ taken together, along with the carbon to which they are bonded, form —C(O)— or —C(S)—;

$R^{18}$ and $R^{19}$ are independently H, alkyl, aralkyl, halide, amido, or ester;

$R^{20}$ is H, alkyl, alkenyl, alkynyl, aryl, cycloalkyl, heterocycloalkyl, aralkyl, heteroaryl, or heteroaralkyl; or any two occurrences of $R^{20}$ on the same substituent can be taken together to form a 4-8 membered optionally substituted ring;

$R^{21}$ is H, alkyl, alkenyl, alkynyl, aryl, cycloalkyl, heterocycloalkyl, aralkyl, heteroaryl, heteroaralkyl or —[C(R$^2$)$_2$]$_p$—R$^{25}$ wherein p is 0-6; or any two occurrences of $R^{21}$ on the same substituent can be taken together to form a 4-8 membered optionally substituted ring;

$R^{23}$ is H, alkyl, alkenyl, alkynyl, aryl, cycloalkyl, heterocycloalkyl, aralkyl, heteroaryl, heteroaralkyl, halide, alkoxyl, aryloxy, acyloxy, silyloxy, nitrile, —C(O)R$^{21}$, —CO$_2$R$^{21}$, —SO$_2$R$^{21}$, and —C(O)N(R$^{21}$)$_2$; and $R^{25}$ is hydroxyl, acylamino, —N(R$^{20}$)COR$^{20}$, —N(R$^{20}$)C(O)OR$^{20}$, —N(R$^{20}$)SO$_2$(R$^{20}$), —COR$^{20}$N(R$^{20}$)$_2$, —OC(O)R$^{20}$N(R$^{20}$)(R$^{20}$), —SO$_2$N(R$^{20}$)(R$^{20}$), —N(R$^{20}$)(R$^{20}$), —COOR$^{20}$, —C(O)N(OH)(R$^{21}$), —OS(O)$_2$OR$^2$, —S(O)$_2$OR$^{20}$, —OP(L)(OR$^{20}$)(OR$^{20}$), —NP(O)(OR$^{20}$)(OR$^{20}$), or —P(O)(OR$^{20}$)(OR$^{20}$).

Further examples of steroidal compounds that can be reduced according to the present invention include compounds of Formula B:

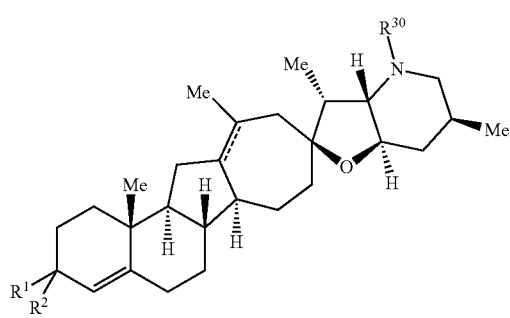

or a pharmaceutically acceptable salt thereof; wherein $R^1$ and $R^2$ taken together with the carbon to which they are bound form a carbonyl;

$R^4$ is H, alkyl, alkenyl, alkynyl, aryl, cycloalkyl, heterocycloalkyl, aralkyl, heteroaryl, heteroaralkyl, haloalkyl, —OR$^5$, —C(O)R$^5$, —CO$_2$R$^5$, —SO$_2$R$^5$, —C(O)N(R$^5$)(R$^5$), —[C(R)$_2$]$_q$—R$^5$, —[(W)—N(R)C(O)]$_q$R$^5$, —[(W)—C(O)]$_q$R$^5$, —[(W)—C(O)O]$_q$R$^5$, —[(W)—OC(O)]$_q$R$^5$, —[(W)—SO$_2$]$_q$R$^5$, —[(W)—N(R$^5$)SO$_2$]$_q$R$^5$, —[(W)—C(O)N(R$^5$)]$_q$R$^5$, —[(W)—O]$_q$R$^5$, —[(W)—N(R)]$_q$R$^5$, —W—NR$^5{}_3{}^4$X$^-$ or —[(W)—S]$_q$R$^5$;

each W is independently a diradical;

each q is independently 1, 2, 3, 4, 5, or 6;

X$^-$ is a halide;

each $R^5$ is independently H, alkyl, alkenyl, alkynyl, aryl, cycloalkyl, heterocycloalkyl, aralkyl, heteroaryl, heteroaralkyl or —[C(R)$_2$]$_p$—R$^6$; wherein p is 0-6; or any two occurrences of $R^5$ can be taken together to form a 4-8 membered optionally substituted ring which contains 0-3 heteroatoms selected from N, O, S, and P;

each $R^6$ is independently hydroxyl, —N(R)COR, —N(R)C(O)OR, —N(R)SO$_2$(R), —C(O)N(R)$_2$, —OC(O)N(R)(R), —SO$_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR); and each R is independently H, alkyl, alkenyl, alkynyl, aryl, cycloalkyl or aralkyl.

Examples of compounds that may be reduced according to the invention include:
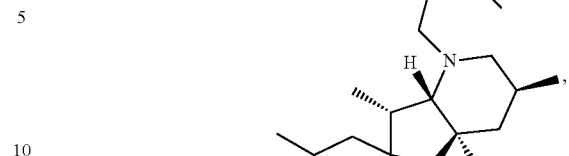
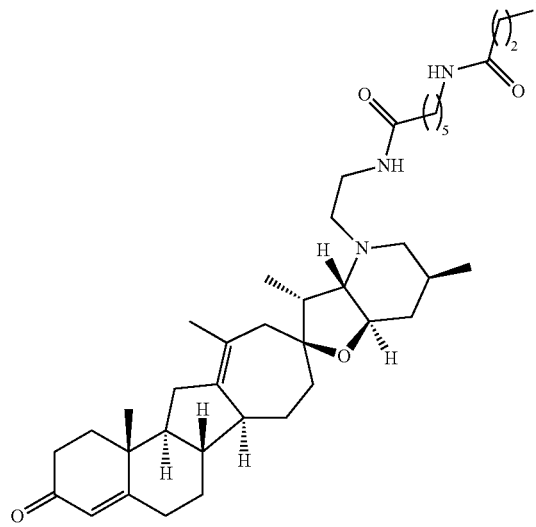
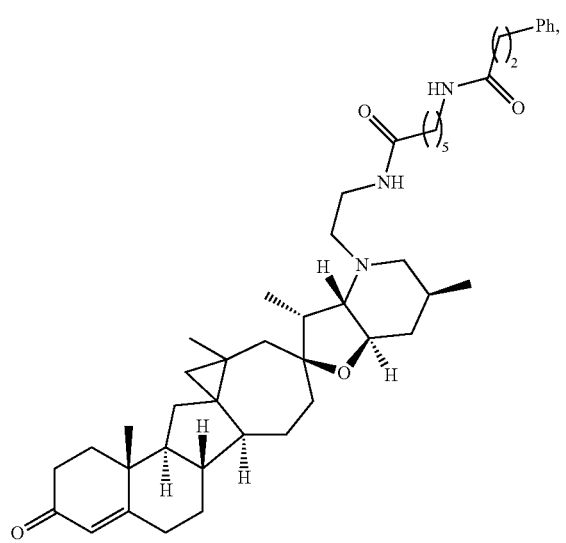
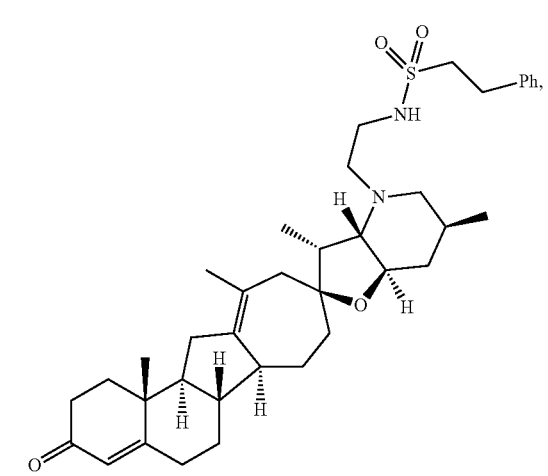
-continued
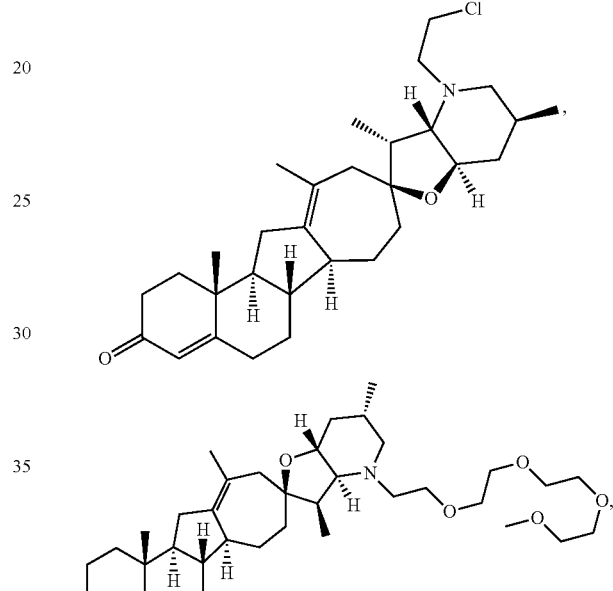
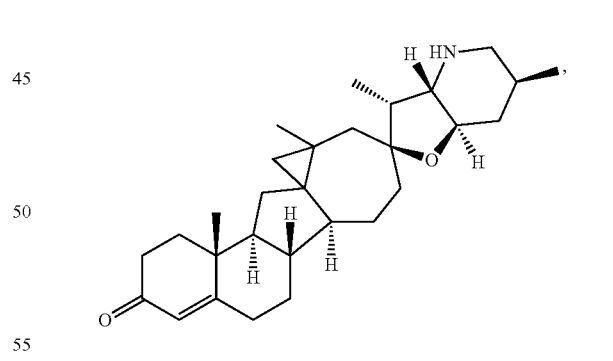
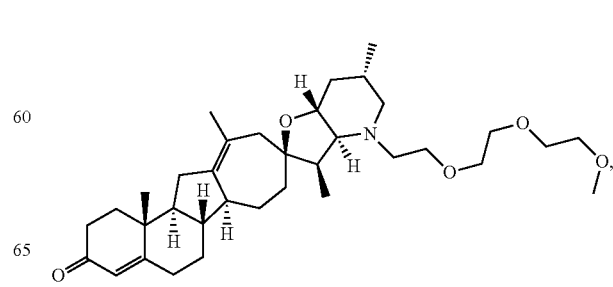

11
-continued
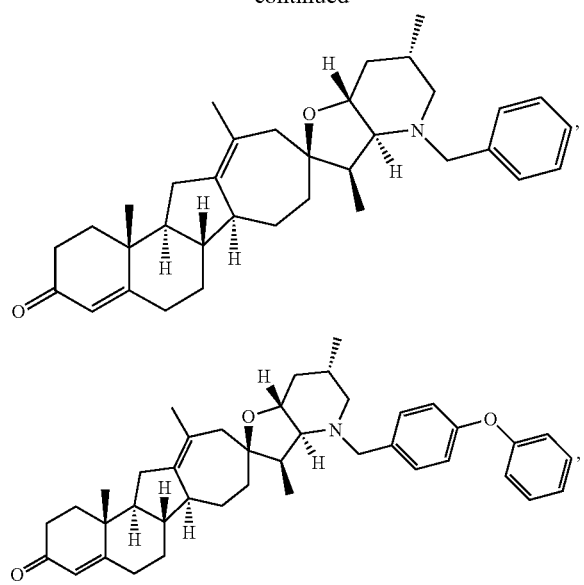
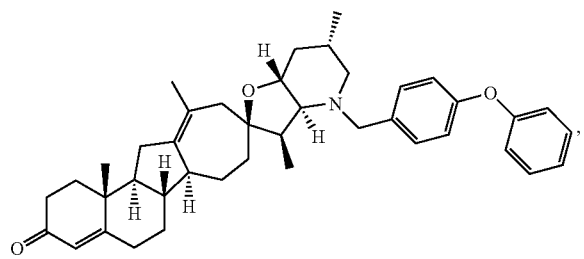
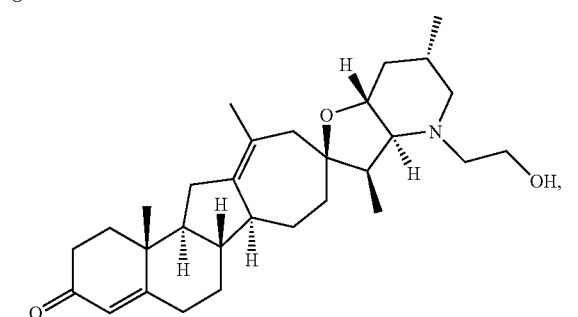
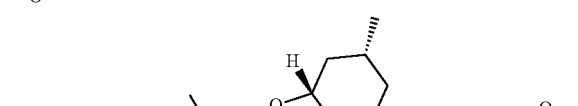
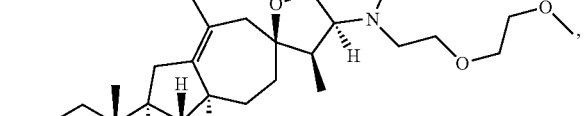
12
-continued
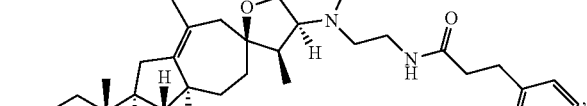
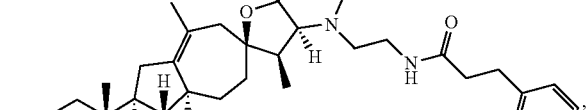
and pharmaceutically acceptable salts thereof.

In one aspect, the invention provides a method of making a mixture of compounds of formulae II and III:

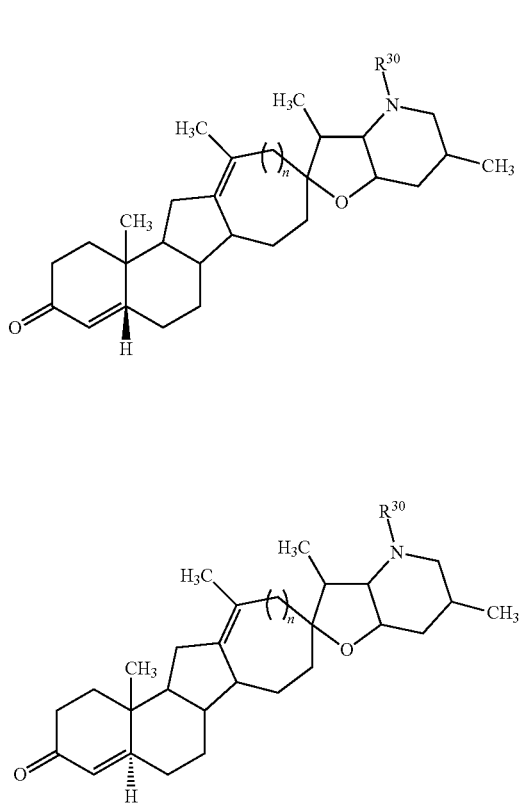

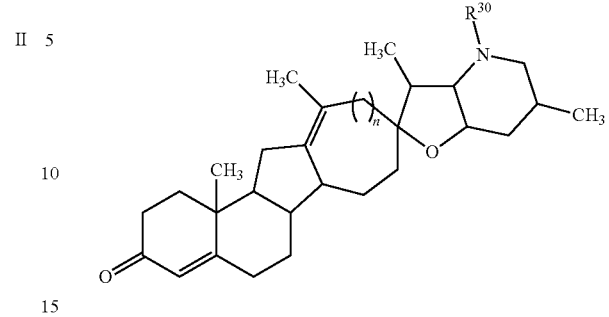

or a pharmaceutically acceptable salt thereof, wherein:

n is 0 or 1;

$R^{30}$ is H, alkyl, alkenyl, alkynyl, aryl, cycloalkyl, heterocycloalkyl, aralkyl, heteroaryl, heteroaralkyl, haloalkyl, —$OR^{31}$, —$C(O)R^{31}$, —$CO_2R^{31}$, —$SO_2R^{31}$, —$C(O)N(R^{31})(R^{31})$, —$[C(R)_2]_q$—$R^{31}$, —[(W)—N(R)C(O)]$_q R^{31}$, —[(W)—C(O)]$_q R^{31}$, —[(W)—C(O)O]$_q R^{31}$, —[(W)—OC(O)]$_q R^{31}$, —[(W)—$SO_2$]$_q R^{31}$, —[(W)—N($R^{31}$)$SO_2$]$_q R^{31}$, —[(W)—C(O)N($R^{31}$)]$_q R^{31}$, —[(W)—O]$_q R^{31}$, —[(W)—N(R)]$_q R^{31}$, —W—(N$R^{31}$)$_3{}^+X^-$ or —[(W)—S]$_q R^{31}$;

W, at each occurrence, independently is an alkylene group;

q, at each occurrence, independently is 1, 2, 3, 4, 5, or 6;

$X^-$ is a halide;

$R^{31}$, at each occurrence, independently is H, alkyl, alkenyl, alkynyl, aryl, cycloalkyl, heterocycloalkyl, aralkyl, heteroaryl, heteroaralkyl or —$[C(R)_2]_p$—$R^{32}$;

or any two occurrences of $R^{31}$ taken together with the atom to which they are bound form an optionally substituted 4-8 membered ring that contains 0-3 heteroatoms selected from N, O and S;

p is 0-6;

each $R^{32}$ is independently hydroxyl, —N(R)COR, —N(R)C(O)OR, —N(R)$SO_2$(R), —C(O)N(R)$_2$, —OC(O)N(R)(R), —$SO_2$N(R)(R), —N(R)(R), —COOR, —C(O)N(OH)(R), —OS(O)$_2$OR, —S(O)$_2$OR, —OP(O)(OR)(OR), —NP(O)(OR)(OR), or —P(O)(OR)(OR); and each R is independently H, alkyl, alkenyl, alkynyl, aryl, cycloalkyl or aralkyl; the method comprising treating a solution or suspension of compound of formula IV:

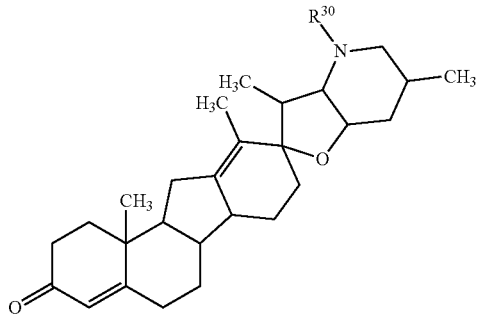

or a pharmaceutically acceptable salt thereof, in a solvent with hydrogen gas in the presence of a catalyst and a substituted pyridine. In some embodiments, an excess of the compound of formula II is produced compared to the compound of formula III (e.g., the ratio of the compound of formula II to compound of formula III is at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1). The substituted pyridine can be a 3-substituted pyridine (e.g., 3-picoline, 3-methoxypyridine, 3-ethylpyridine, 3-n-butylpyridine, 3-isobutylpyridine, 3-hydroxypyridine, 3-aminopyridine, or 3-dimethylaminopyridine).

In some embodiments, the solvent is the substituted pyridine (e.g., 3-picoline). The catalyst can be a palladium catalyst (e.g., palladium on carbon). In some embodiments, n is 0, i.e., the compound of formula IV has the following structure:

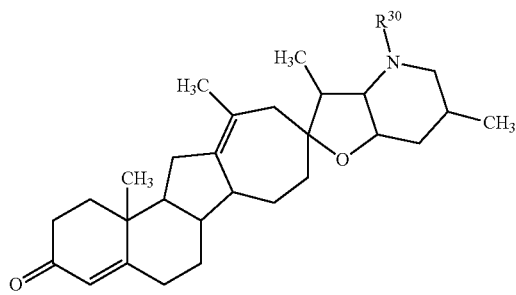

In other embodiments, n is 1, i.e., the compound of formula IV has the following structure:

In some embodiments, $R^{30}$ is H, i.e., the compound of formula IV has one of the following structures:

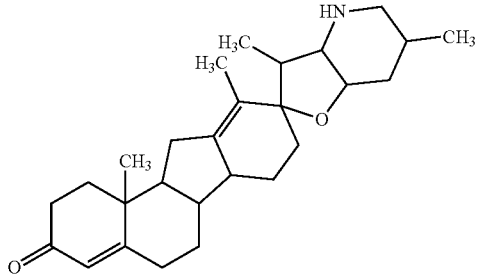

or

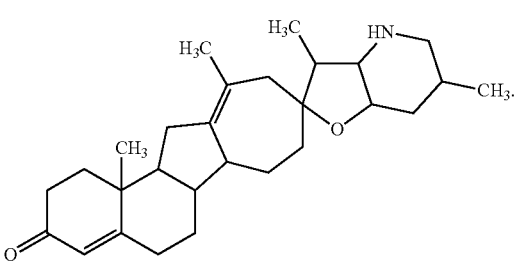

In some embodiments, the compounds of formulae IV, II and III have the following absolute chemistry:

IV

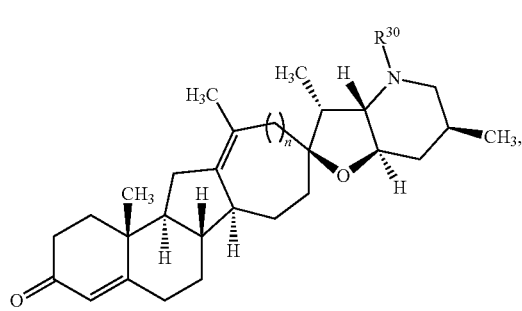

II

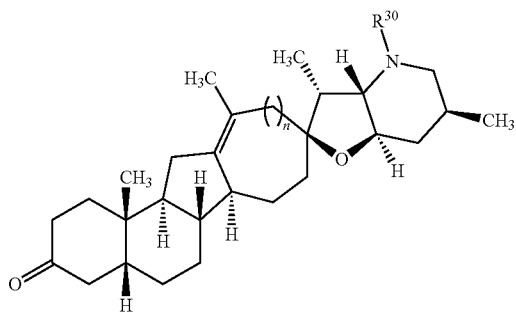

and

III

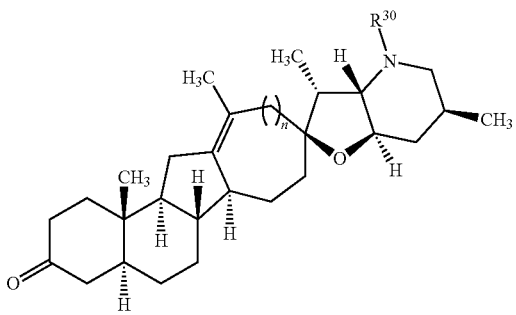

In another aspect, the invention provides a method of making a mixture of compounds V and VI:

V

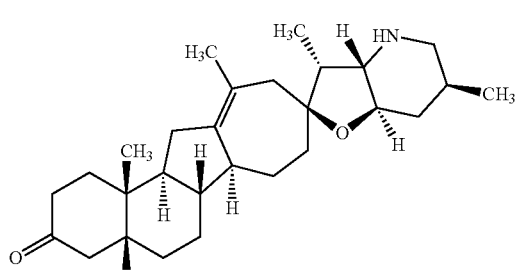

VI

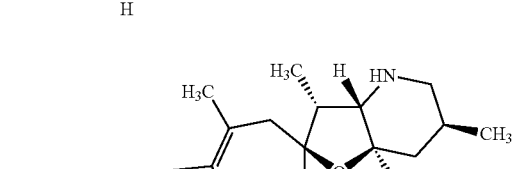

or a pharmaceutically acceptable salt thereof, the method comprising treating a solution or suspension of compound VII:

VII

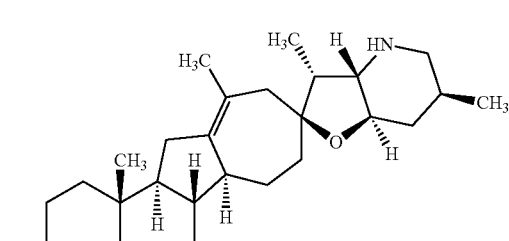

or a pharmaceutically acceptable salt thereof, in a solvent with hydrogen gas in the presence of a palladium catalyst and a substituted pyridine. In some embodiments, an excess of the compound of formula V is produced compared to the compound of formula VI (e.g., the ratio of the compound of formula V to compound of formula VI is at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1). The substituted pyridine can be a 3-substituted pyridine (e.g., 3-picoline, 3-methoxypyridine, 3-ethylpyridine, 3-n-butylpyridine, 3-isobutylpyridine, 3-hydroxypyridine, 3-aminopyridine, or 3-dimethylaminopyridine). Alternatively, the substituted pyridine can be a 4-substituted pyridine (e.g., 4-picoline, 4-methoxypyridine, 4-aminopyridine, or 4-dimethylaminopyridine). In some embodiments, the solvent is the substituted pyridine (e.g., 3-picoline). The catalyst can be a palladium catalyst (e.g., palladium on carbon). The method can include the further steps of adding an aqueous solution of an acid (e.g., HCl, HBr, HI, H₂SO₄, H₃PO₄, methanesulfonic acid, ethanesulfonic acid, benzenesulfonic acid, toluenesulfonic acid, citric acid, benzoic acid, formic acid, acetic acid, propionic acid, gluconic acid, lactic acid, oxalic acid, trifluoroacetic acid, or tartaric acid) and isolating the salt of compounds V and/or VI. In some embodiments, the citric acid salts of compounds V and/or VI are prepared and isolated.

In another aspect, the method provides compounds of formulae IX and X:

IX

X and mixtures thereof, wherein X⁻ is the conjugate base of a pharmaceutically acceptable acid (e.g., chloride, bromide, sulfate, methanesulfonate or citrate). In some embodiments, X⁻ is citrate. When compounds of formulae IX and X are present in a mixture, an excess of compound IX can be present compared to compound X. For example, the ratio of the compound of formula IX to compound of formula X can be at least about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1.

In another aspect, the invention provides a method of making a compound of formula XV:

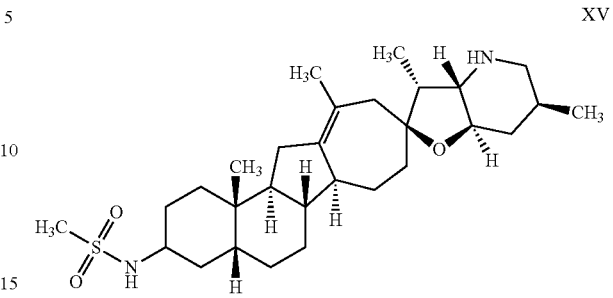

XV comprising the steps of:
(a) treating a compound of formula IX:

IX wherein X⁻ is the conjugate base of a pharmaceutically acceptable salt (e.g., chloride, bromide, sulfate, methanesulfonate or citrate), with an amine protecting reagent to produce a compound of formula XI:

XI wherein PG is an amine protecting group;

(b) treating the compound of formula XI with a reducing agent to produce an alcohol of formula XII:

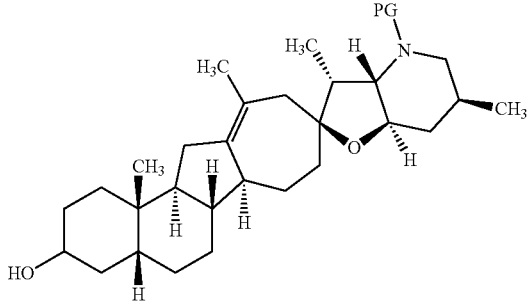

(c) converting the alcohol of formula XII to an amine of formula XIII:

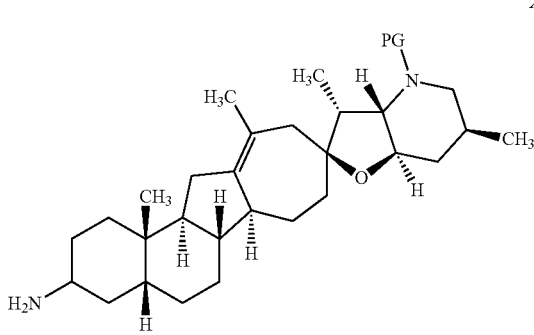

(d) treating the amine of formula XIII with a sulfonylating agent (e.g., methanesulfonyl chloride) to produce a sulfonamide of formula XIV:

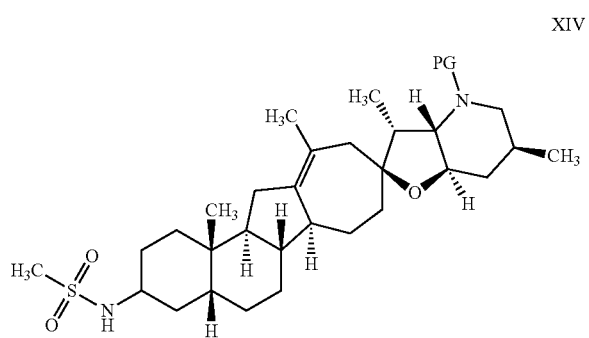

and (e) deprotecting the amine of the compound of formula XIV to produce the compound of formula XV.

The protecting group (PG) can be any suitable amine protecting group known in the art, including carbamates (e.g., carbobenzyloxy (Cbz), t-butyloxycarbonyl (BOC), allyloxycarbonyl (Alloc), 9-fluoenylmethyl (Fmoc), and the like), amide-forming groups (e.g., acetyl, trifluoroacetyl, benzoyl, and the like), silyl groups and benzyl. Suitable amine protecting reagents include chlorides, acid chlorides, anhydrides (including mixed anhydrides) and other activated species that will react with the amine and deliver the protecting group. Examples include BOC-Cl, (BOC)$_2$O, Cbz-Cl, (Cbz)$_2$O, Cbz-O-benzotriazole, Alloc-Cl, (Alloc)$_2$O, Fmoc-Cl, (Fmoc)$_2$O, benzylchloride, and the like. See, e.g., Greene, *Protective Groups in Organic Synthesis*.

In step (b), the reducing agent can be any reducing agent known in the art that will reduce a ketone to an alcohol. Examples of suitable reducing agents include boron reducing agents (e.g., potassium tri-sec-butylborohydride, sodium borohydride), and metallic hydrides (e.g., lithium aluminum hydride). See, e.g., March, *Advanced Organic Chemistry*.

Step (c) can comprise the steps of (1) converting the alcohol to a leaving group to produce a compound of formula XVI:

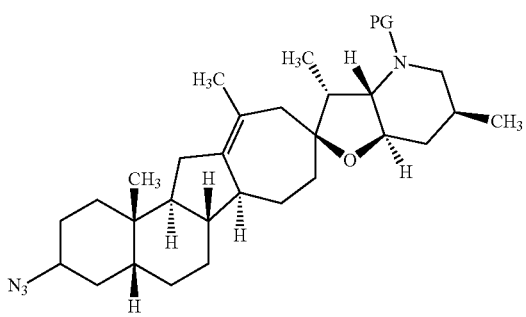

wherein LG is a leaving group, followed by (2) treating the compound of formula XVI with an azide reagent to produce a compound of formula XVII:

and (3) treating the compound of formula XVII with a reducing agent to form the amine of formula XIII.

The leaving group (LG) can be a sulfonate group (e.g., methanesulfonate, benzenesulfonate, toluenesulfonate, and the like), a halogen (e.g., Cl, Br) or any other suitable leaving group known in the art. The leaving group can be formed by treatment with the corresponding sulfonyl chloride (e.g., methanesulfonyl chloride) or with an acid halide (e.g., HBr). See, e.g., March, *Advanced Organic Chemistry*.

The azide reagent can be, for example, sodium azide, potassium azide, methanesulfonyl azide, p-toluenesulfonyl azide, p-acetamidobenzenesulfonyl azide, 4-carboxybenzenesulfonyl azide, p-dodecylbenzenesulfonyl azide, or trimethylsilyl azide. See, e.g., March, *Advanced Organic Chemistry*. In some embodiments, the azide reagent is sodium azide.

Any suitable reducing agent known in the art may be used to reduce the azide of the compound of formula XVII to the amine of formula XIII. Examples of reducing agents include lithium aluminum hydride, sodium borohydride, and triphenylphosphine. The azide can also be reduced to the amine by catalytic hydrogenation. See, e.g., March, *Advanced Organic Chemistry*. In some embodiments, the azide is reduced using triphenylphosphine.

The amine protecting group PG can be removed by standard conditions known in the art. The particular deprotection conditions will vary depending upon the nature of the protecting group. For example, a Cbz group can be removed by hydrogenation using a catalyst (e.g., a palladium catalyst such as Pd/C or palladium black) and hydrogen gas or another hydrogen donor (e.g., cyclohexene, 1,4-cyclohexadiene, formic acid). See, e.g., Greene, *Protective Groups in Organic Synthesis*.

The order of one or more steps in the synthesis of compound XV from compound IX can be changed, provided that the change results in the complete synthesis of compound XV. For example, introduction of the amine protecting group PG can occur at any time in the synthesis prior to reduction of the azide XVII to produce amine XIII. Compound IX can be treated with a reducing agent to produce an alcohol of formula XIIa:

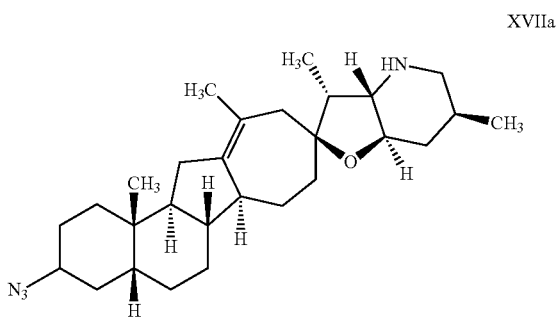

Compound XVIIa can then be treated with the amine protecting group to form a compound of formula XVII.

In some embodiments, the method further comprises the step of treating the compound of formula XV with an acid to produce a compound of formula XIX:

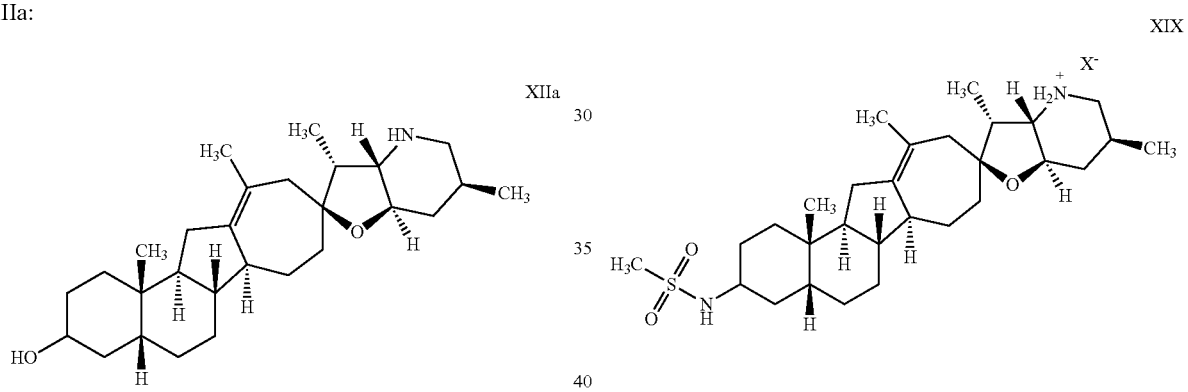

Compound XIIa can then be treated with the amine protecting agent to form compound XII. Alternatively, the alcohol moiety of compound XIIa can be converted to a leaving group to produce a compound of formula XVIa:

wherein X⁻ is the conjugate base of a pharmaceutically acceptable acid (e.g., chloride, bromide, sulfate, methanesulfonate or citrate). In some embodiments, the acid is HCl and X⁻ is chloride.

In some embodiments, the compound of formula XV has the following absolute stereochemistry:

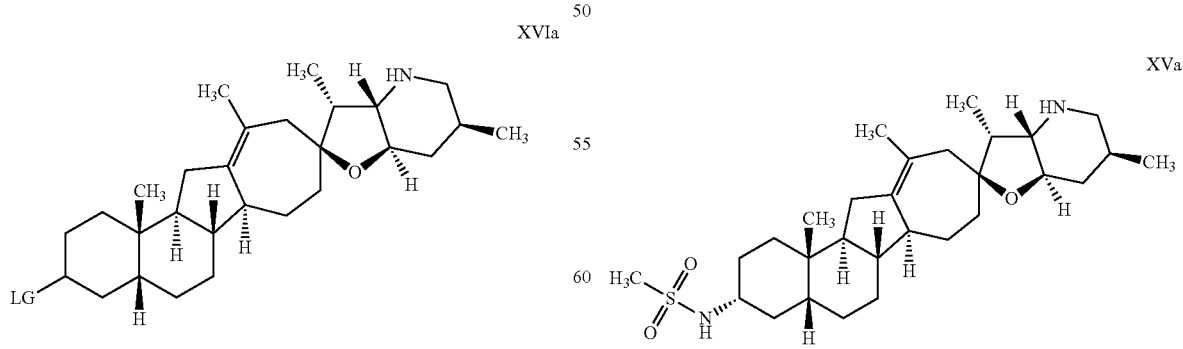

Compound XVIa can then be treated with the amine protecting agent to form compound XVI. Alternatively, compound XVIa can be treated with an azide reagent to produce a compound of formula XVIIa:

In other embodiments, the method produces a mixture of compounds having the structures with the following absolute stereochemistry:

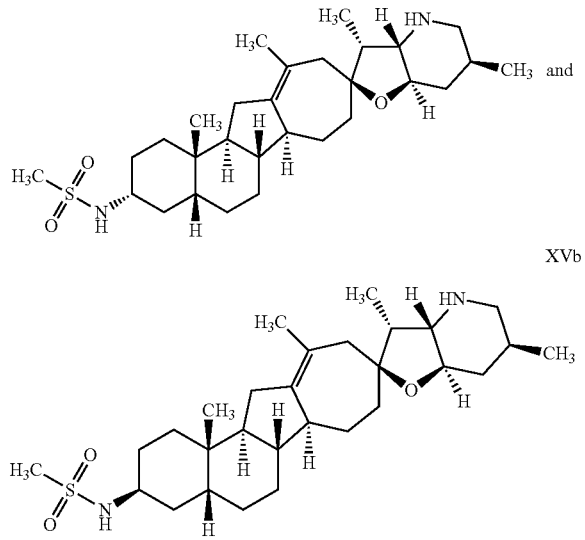

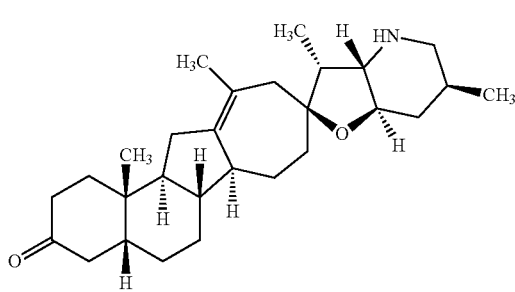

In some instances, compound XVa is produced in excess of compound XVb (e.g., the ratio of XVa to XVb is about 2:1, about 3:1, about 5:1, about 10:1, about 20:1, about 25:1, about 30:1, about 40:1, about 50:1, about 60:1, about 70:1, about 80:1, about 90:1, about 95:1, or greater than about 99:1).

In another aspect, the invention provides a mixture of a compound of formula V:

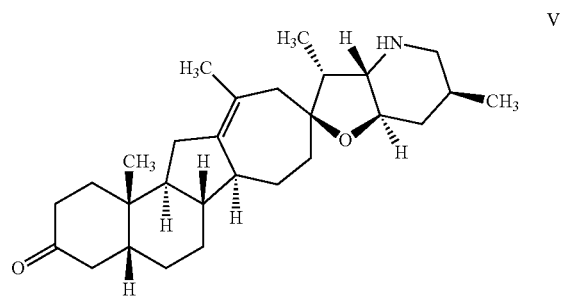

or a pharmaceutically acceptable salt thereof, and a compound of formula 2a or a pharmaceutically acceptable salt thereof:

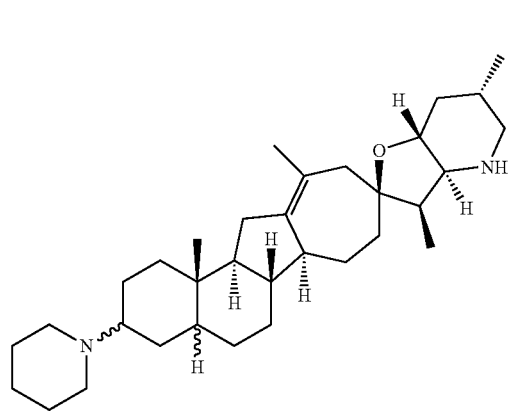

In some embodiments, compound 2a is present in less than about 10%, about 5%, about 2%, about 1%, about 0.5%, about 0.1%, or about 0.01%.

In another aspect, the invention provides a mixture of a compound of formula V:

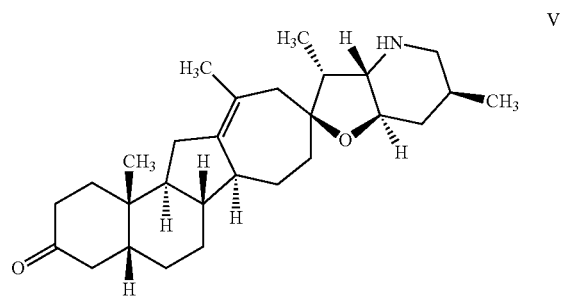

or a pharmaceutically acceptable salt thereof, and a compound of formula 2b or a pharmaceutically acceptable salt thereof:

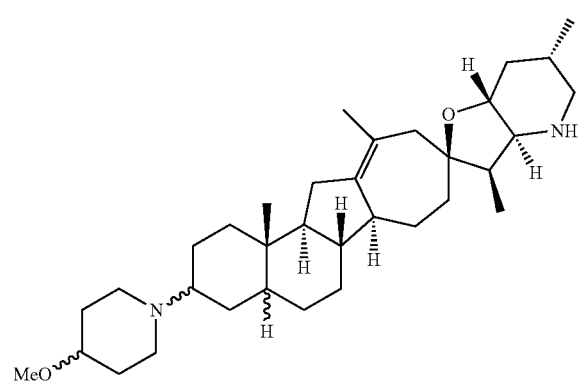

In some embodiments, compound 2b is present in less than about 10%, about 5%, about 2%, about 1%, about 0.5%, about 0.1%, or about 0.01%.

In yet another aspect, the invention provides a mixture of a compound of formula V:

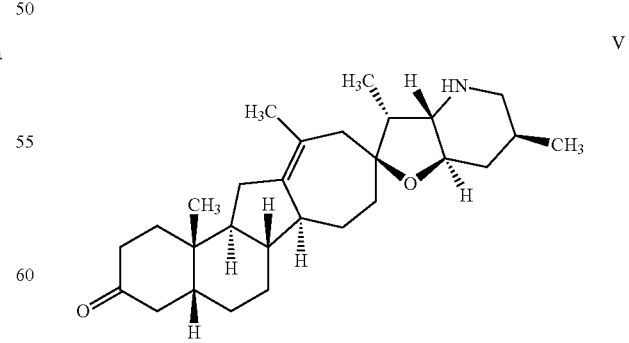

or a pharmaceutically acceptable salt thereof, and a compound of formula 2c or a pharmaceutically acceptable salt thereof:

2c

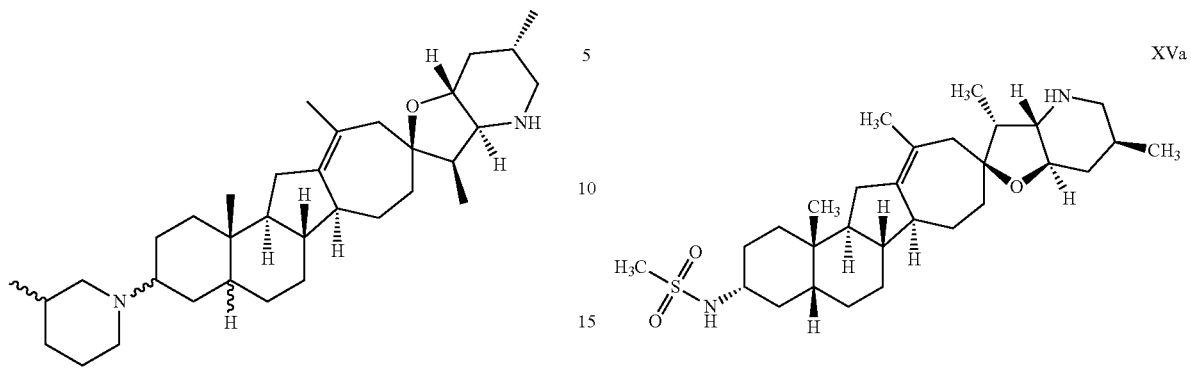

In some embodiments, compound 2c is present in less than about 10%, about 5%, about 2%, about 1%, about 0.5%, about 0.1%, or about 0.01%.

In another aspect, the invention provides a mixture of compounds V and VI:

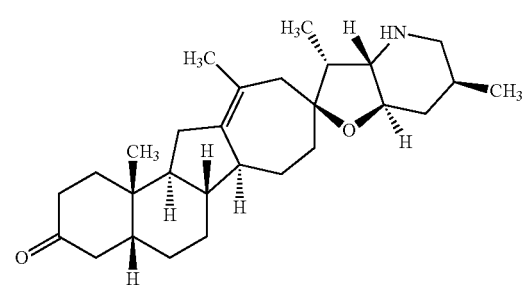

V

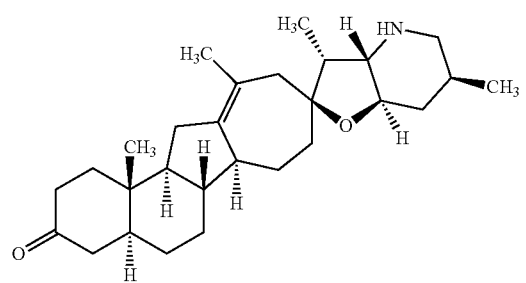

VI or a pharmaceutically acceptable salt thereof, and one of compounds 2a, 2b or 2c or a pharmaceutically acceptable salt thereof. In some embodiments, compound 2a, 2b or 2c is present in less than about 10%, about 5%, about 2%, about 1%, about 0.5%, about 0.1%, or about 0.01%.

In another aspect, the invention provides a mixture of compound XVa:

XVa or a pharmaceutically acceptable salt thereof, and one of compounds 2a, 2b or 2c or a pharmaceutically acceptable salt thereof. In some embodiments, compound 2a, 2b or 2c is present in less than about 10%, about 5%, about 2%, about 1%, about 0.5%, about 0.1%, or about 0.01%. In some embodiments, the pharmaceutically acceptable salt is a hydrochloride salt.

The term "heteroatom" refers to an atom of any element other than carbon or hydrogen. Illustrative heteroatoms include nitrogen, oxygen, and sulfur.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 10 or fewer carbon atoms in its backbone (e.g., $C_1$-$C_{10}$ for straight chain, $C_3$-$C_{10}$ for branched chain). In certain embodiments, a straight chain or branched chain alkyl has about 6 or fewer carbon atoms in its backbone (e.g., $C_1$-$C_6$ for straight chain, $C_3$-$C_6$ for branched chain). Cycloalkyls have from about 3 to about 10 carbon atoms in their ring structure, e.g., about 3, 4, 5, 6 or 7 carbons in the ring structure. Alkyl groups, unless otherwise specified, may optionally be substituted by replacing one or more hydrogens with a suitable substituent. Suitable substituents for alkyl groups include halogen, =O, =N—CN, =N—OR', =NR', OR', NR'$_2$, SR', SO$_2$R', SO$_2$NR'$_2$, NR'SO$_2$R', NR'CONR'$_2$, NR'COOR', NR'COR', CN, COOR', CONR'$_2$, OOCR', COR', and NO$_2$, wherein each R' is independently H, $C_1$-$C_6$ alkyl, $C_2$-$C_6$ heteroalkyl, $C_1$-$C_6$ acyl, $C_2$-$C_6$ heteroacyl, $C_6$-$C_{10}$ aryl, $C_5$-$C_{10}$ heteroaryl, $C_7$-$C_{12}$ arylalkyl, or $C_6$-$C_{12}$ heteroarylalkyl, each of which is optionally substituted with one or more groups selected from halo, $C_1$-$C_4$alkyl, $C_1$-$C_4$ heteroalkyl, $C_1$-$C_6$ acyl, $C_1$-$C_6$ heteroacyl, hydroxy, amino, and =O; and wherein two R' on the same substituent or on adjacent atoms can be linked to form a 3-7 membered ring optionally containing up to three heteroatoms selected from N, O and S.

Unless the number of carbons is otherwise specified, "lower alkyl" refers to an alkyl group, as defined above, having from one to six carbon atoms in its backbone structure. Likewise, "lower alkenyl" and "lower alkynyl" have similar chain lengths.

The terms "alkenyl" and "alkynyl" refer to straight-chain or branched unsaturated aliphatic groups that contain at least one double or triple bond respectively and may contain a mixture of both double and triple bonds. Alkenyl and alkynyl groups have about 10 or fewer carbon atoms in their backbones (e.g., $C_2$-$C_{10}$ for straight chain and $C_4$-$C_{10}$ for branched chain). In certain embodiments, alkenyl and alkynyl groups have about 6 or fewer carbon atoms in their backbones (e.g., $C_1$-$C_6$ for straight chain and $C_4$-$C_6$ for branched chain). Alkenyl and alkynyl groups can be optionally substituted by the same substituents described above for alkyl groups.

The term "aryl" refers to 5-, 6- and 7-membered single-ring aromatic groups that may include from zero to four heteroatoms. Examples of aryl include benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl". The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes fused polycyclic ring systems wherein at least one of the rings is aromatic, e.g., the other cyclic rings may be cycloalkyls, cycloalkenyls, cycloalkynyls, aryls and/or heterocyclyls.

The term "aralkyl" refers to an alkyl group substituted with an aryl group (e.g., an aromatic or heteroaromatic group).

The terms "heterocycle", "heteroaryl", or "heterocyclic group" refer to 3- to 10-membered ring structures, alternatively 3- to 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" refers to an aromatic or non-aromatic ring in which each atom of the ring is carbon.

The terms "amine", "amino" and "ammonium" refer to both unsubstituted and substituted amines, e.g., a moiety that may be represented by the general formulas:

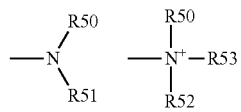

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure, one or more of which may be additional heteroatoms selected from N, O and S; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$— R61. Thus, the term "alkylamine" includes an amine group, as defined above, having a substituted or unsubstituted alkyl attached thereto, i.e., at least one of R50 and R51 is an alkyl group.

The term "acylamino" refers to a moiety that may be represented by the general formula:

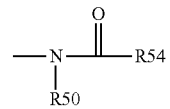

wherein R50 is as defined above, and R54 represents a hydrogen, an alkyl, an alkenyl or —$(CH_2)_m$—R61, where m and R61 are as defined above.

The term "amido" refers to an amino-substituted carbonyl and includes a moiety that may be represented by the general formula:

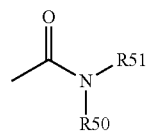

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" refers to such moieties as may be represented by the general formulas:

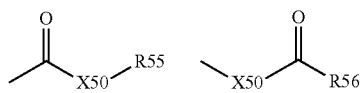

wherein X50 is a bond or represents an oxygen or a sulfur, and R55 and R56 represents a hydrogen, an alkyl, an alkenyl, —$(CH_2)_m$—$_R$61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C=O)NRR', where R and R' are independently H, aliphatic groups, aryl groups or heteroaryl groups.

The term "oxo" refers to a carbonyl oxygen (=O).

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

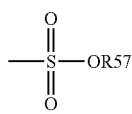

in which R57 is an electron pair, hydrogen, alkyl, cycloalkyl, or aryl.

The term "sulfate" is art recognized and includes a moiety that may be represented by the general formula:

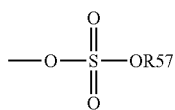

in which R57 is as defined above.

The term "sulfonamido" is art recognized and includes a moiety that may be represented by the general formula:

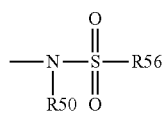

in which R50 and R56 are as defined above.

The term "sulfamoyl" is art-recognized and refers to a moiety that may be represented by the general formula:

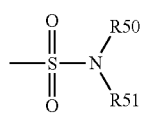

in which R50 and R51 are as defined above.

The term "sulfonyl" is art-recognized and refers to a moiety that may be represented by the general formula:

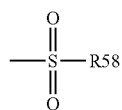

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

in which R58 is defined above.

The definition of each expression, e.g. alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms (e.g., nitrogen) may have hydrogen substituents and/or any permissible substituents of organic compounds described herein which satisfy the valences of the heteroatoms.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The invention now being generally described, it will be more readily understood by reference to the following examples, which are included merely for purposes of illustration of certain aspects and embodiments of the present invention, and are not intended to limit the invention.

EXAMPLES

In experiments where the reduction products were UV active, the products were identified and the β/α ratio was determined using HPLC. General HPLC methods are as follows:

Column: Symmetry $C_{18}$ 5 um column, 4.6×150 mm
Solvent A: 0.1% aqueous trifluoroacetic acid
Solvent B: 0.1% trifluoroacetic acid in acetonitrile
Method 1

| Time (min.) | % Solvent A | % Solvent B |
| --- | --- | --- |
| 0.00 | 90.0 | 10.0 |
| 2.00 | 90.0 | 10.0 |
| 20.00 | 40.0 | 60.0 |
| 22.0 | 5.0 | 95.0 |
| 23.0 | 5.0 | 95.0 |
| 24.0 | 90.0 | 10.0 |
| 30.0 | 90.0 | 10.0 |

Signal: 215 nm

Method 2

| Time (min.) | % Solvent A | % Solvent B |
|---|---|---|
| 0.00 | 70.0 | 30.0 |
| 2.00 | 70.0 | 30.0 |
| 12.0 | 5.0 | 95.0 |
| 13.0 | 5.0 | 95.0 |
| 13.10 | 70.0 | 30.0 |
| 15.0 | 70.0 | 30.0 |
| 0.00 | 70.0 | 30.0 |

Signal: 290 nm

Example 1

Reduction of Steroidal Enones

General Method:

The steroidal enone (100 mg) and 5% palladium on carbon (Johnson Matthey type A503023-5, 20 mg) were charged to a reaction vessel and 1 mL of solvent (3-picoline, pyridine or THF) was added. The reaction mixture was stirred and alternately degassed under vacuum and charged with hydrogen three times. The reaction mixture was stirred under balloon-pressure hydrogen until HPLC indicated the reaction was complete. The reaction mixture was filtered and the filtrate was analyzed by LCMS and HPLC. In those instances where the reduction products were UV active, the β/α ratio was determined by comparing the area under the HPLC curve for each product (retention times of each reaction product were compared against known standards). When the reduction products were not UV active (e.g., the reduced testosterone products), the β/α ratio was determined by integrating the LCMS peaks. The results are summarized in Table 1 below.

TABLE 1

| Steroid enone | β/α ratio in THF | β/α ratio in pyridine | β/α ratio in 3-picoline |
|---|---|---|---|
| Cyclopamine enone* | 5:1 | 10:1 | 24:1 |
| 4-Androstene-3,17-dione | 3:1 | 16:1 | 25:1 |
| Testosterone** | 13:1 | 100:1 | 100:1 |
| Cortisone | 0.7:1 | 4:1 | 8:1 |
| Progesterone | 3:1 | 29:1 | 48:1 |
| Adrenosterone | 0.8:1 | 1:1 | 1.2:1 |
| Prednisone | 1.7:1 | 1.9:1 | 1.2:1 |

*Cyclopamine enone has the following structure:

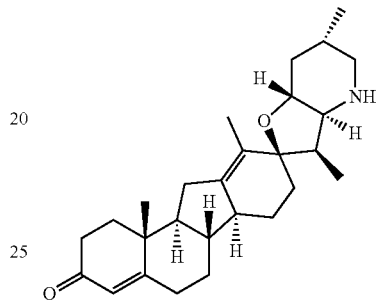

**The β/α ratio for the testosterone reduction products was determined by LCMS.

These results indicate that catalytic reduction of steroidal compounds using the 3-pyridine solvent 3-picoline generally increases the ratio of β/α reduction products. It is noted that the increase in selectivity was not shown for the reduction of prednisone. It was observed that the 1,2-ene of prednisone was reduced nearly twice as fast as the 4,5-ene:

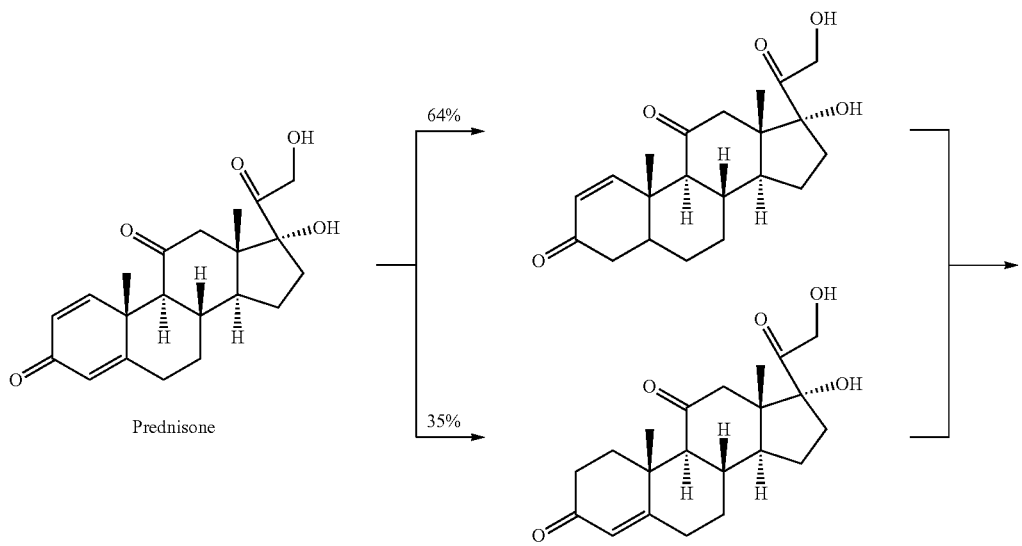

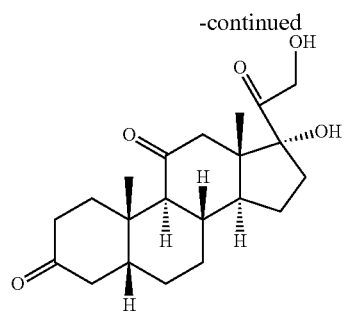
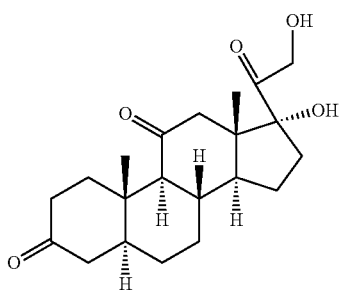

This difference in the rate of initial enone reduction may be responsible for the drop in β/α selectivity for the fully reduced products (and also the difference in selectivity between prednisone and cortisone).

Example 2

Solvents

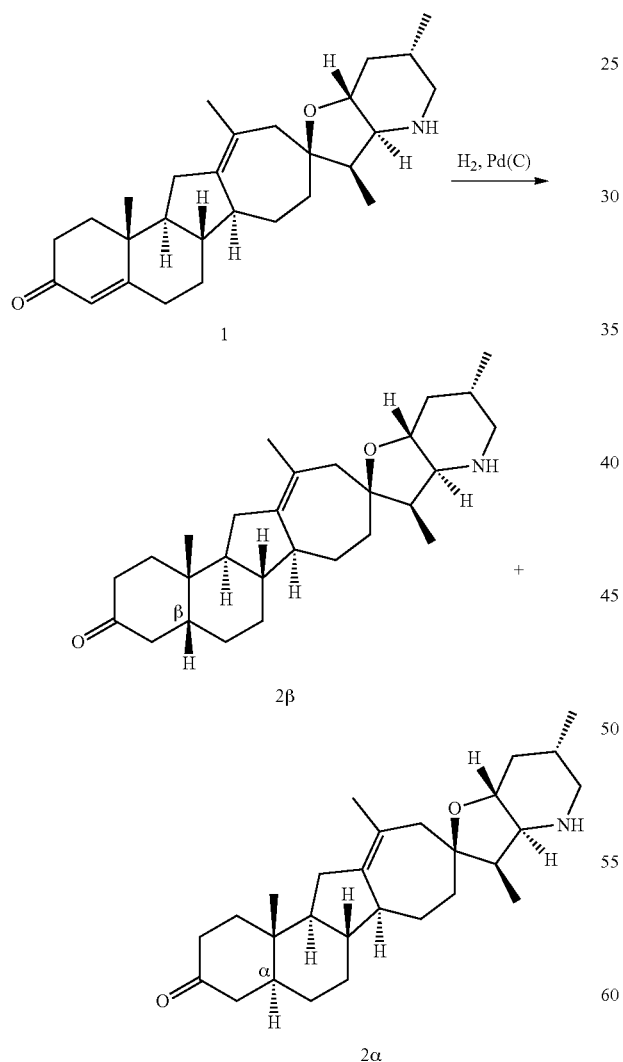

General method:

Compound 1 (~100 mg) and Degussa type E101 10% palladium on carbon (~20 mg) were charged to a reaction vessel and 1 mL of solvent was added. The reaction mixture was stirred and alternately degassed under vacuum and charged with hydrogen (balloon pressure) three times. The reaction mixture was stirred under balloon-pressure hydrogen until HPLC indicated the reaction was complete. The reaction mixture was filtered and the filtrate was analyzed by LCMS and HPLC. The β/α ratio was determined by comparing the area under the HPLC curve for each product (retention times of each reaction product were compared against known standards). The results are summarized in Table 2 below.

TABLE 2

| Solvent | β/α Product Ratio |
| --- | --- |
| Pyridine | 16:1 |
| 2,6-Lutidine | 9:1 |
| 2-Methoxypyridine | 11:1 |
| 3-Methoxypyridine | 54:1 |
| 4-Methoxypyridine | 32:1 |
| DMAP | 9:1 |
| 2-Picoline (2-methylpyridine) | 8:1 |
| 3-Picoline | 53:1 |
| 4-Picoline | 31:1 |
| 3-Acetoxypyridine | 27:1 |
| 3-isoButylpyridine | 15:1 |
| 3-Ethylpyridine | 40:1 |
| Ethyl-3-pyridylacetate | 24:1 |
| 3,5-Lutidine | 27:1 |
| 4-tertButylpyridine | 33:1 |

These results indicate that reducing the enone double bond of Compound 1 in 3-substituted pyridine solvents (e.g., 3-methoxypyridine, 3-picoline, 3-ethylpyridine) generally increases the β/α ratio of the reduction products, particularly compared to unsubstituted pyridine and 2-substituted pyridine solvents. The results also show that among isomeric pyridine solvents, (e.g., 2-, 3-, and 4-picoline and 2-, 3-, and 4-methoxypyridine) the 3-substituted pyridines provide the greatest selectivity for the β reduction product.

Example 3

Catalysts

Experiments were carried out as described in Example 2 above, using Compound 1 as substrate and 3-picoline as solvent. The results are summarized in Table 3 below.

TABLE 3

| Catalyst | β/α Product Ratio |
| --- | --- |
| 10% Degussa Pd/C | 53:1 |
| 5% Pd/C (JM type A401102-5) | 35:1 |
| 5% Pd/C (JM type A109047-5) | 35:1 |
| 5% Pd/C (JM type A405032-5) | 36:1 |

TABLE 3-continued

| Catalyst | β/α Product Ratio |
| --- | --- |
| 5% Pd/C (JM type A405038-5) | 32:1 |
| 5% Pd/C (JM type A503023-5) | 71:1 |
| 5% Pd/C (JM type A503032-5) | 49:1 |
| 5% Pd/C (JM type A503038-5) | 40:1 |
| 5% Pd/C (JM type A102023-5) | 63:1 |
| 5% Pd/C (JM type A102038-5) | 32:1 |
| 5% Pd/C (JM type A302011-5) | 24:1 |
| 5% Pd/C (JM type A302084-5) | 28:1 |
| 4% Pd, 1% Pt on carbon (JM type E101049-4/1) | 33:1 |

These results indicate that the increased β selectivity obtained by using the substituted pyridine solvent is maintained when a variety of hydrogenation catalysts are employed.

Example 4

Co-solvents

Experiments were carried out as described in Example 2 above, using Compound 1 as substrate and various palladium catalysts in neat 3-picoline or a 10% solution (v/v) of 3-picoline in THF. The results are summarized in Table 4 below.

TABLE 4

| Catalyst | 3-Picoline β/α Product Ratio | 3-Picoline/THF β/α Product Ratio |
| --- | --- | --- |
| 10% Degussa Pd/C | 53:1 | 22:1 |
| 5% Pd/C (JM type A401102-5) | 35:1 | 14:1 |
| 5% Pd/C (JM type A109047-5) | 35:1 | 17:1 |
| 5% Pd/C (JM type A503023-5) | 71:1 | 15:1 |
| 5% Pd/C (JM type A503032-5) | 49:1 | 26:1 |
| 5% Pd/C (JM type A503038-5) | 40:1 | 16:1 |
| 5% Pd/C (JM type A102023-5) | 63:1 | 26:1 |
| 5% Pd/C (JM type A102038-5) | 32:1 | 20:1 |
| 5% Pd/C (JM type A302011-5) | 24:1 | 15:1 |
| 5% Pd/C (JM type A302084-5) | 28:1 | 16:1 |

Further experiments were carried out as described in Example 2 above, using Compound 1 as substrate and Degussa type E101 10% palladium on carbon or Pearlman's catalyst (palladium hydroxide on carbon) in neat 4-methoxypyridine (4-OMePy) or a 10% solution (v/v) of 4-methoxypyridine in a co-solvent. The results are summarized in Table 5 below.

TABLE 5

| Solvent | 10% Pd/C β/α ratio | Pearlman's cat. β/α ratio |
| --- | --- | --- |
| 4-OMePy | 32:1 | 27:1 |
| 10% 4-OMePy in THF | 20:1 | 18:1 |
| 10% 4-OMePy in EtOAc | 14:1 | 12:1 |
| 10% 4-OMePy in Toluene | 11:1 | 11:1 |
| 10% 4-OMePy in EtOH | 13:1 | 14:1 |

These results indicate that, while the use of neat substituted pyridine as solvent generally yields the highest β/α product ratio, the β reduction product continues to be favored when the substituted pyridine is used in conjunction with a co-solvent. In addition, these results indicate that the β reduction product continues to be favored when a variety of combinations of co-solvent and hydrogenation catalyst are employed.

Example 5

Co-solvents

Experiments were carried out as described in Example 2 above, using Compound 1 as substrate and Degussa type E101 10% palladium on carbon as catalyst in neat 4-methoxypyridine (4-OMePy) or a 10% solution (v/v) of 4-methoxypyridine in a co-solvent. The results are summarized in Table 6 below.

TABLE 6

| Solvent | β/α Ratio |
| --- | --- |
| 4-OMePy | 32:1 |
| 10% 4-OMePy in THF | 20:1 |
| 10% 4-OMePy in Dioxane | 17:1 |
| 10% 4-OMePy in MTBE | 16:1 |
| 10% 4-OMePy in DME | 15:1 |
| 10% 4-OMePy in EtOAc | 14:1 |
| 10% 4-OMePy in Acetone | 13:1 |
| 10% 4-OMePy in EtOH | 13:1 |
| 10% 4-OMePy in Toluene | 11:1 |

These results indicate that, while the use of neat substituted pyridine as solvent generally yields the highest β/α product ratio, the β reduction product continues to be favored when the substituted pyridine is used in conjunction with a co-solvent.

Example 6

Side-products

Side-product 2a was identified by HPLC and LCMS from the reduction of Compound 1 with Pd/C in the presence of pyridine:

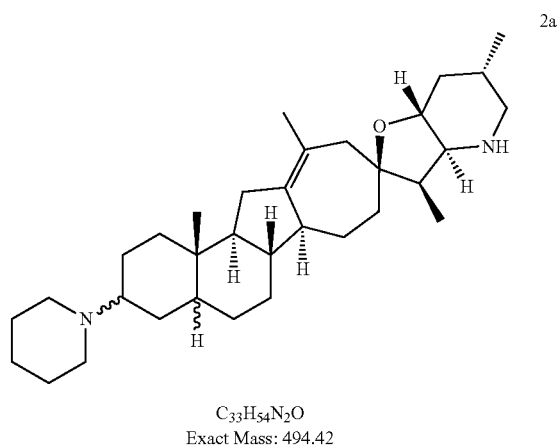

2a $C_{33}H_{54}N_2O$
Exact Mass: 494.42

Similarly, side-products 2b and 2c were identified from the reduction of Compound 1 with Pd/C in the presence of 4-methoxypyridine and 3-picoline, respectively:

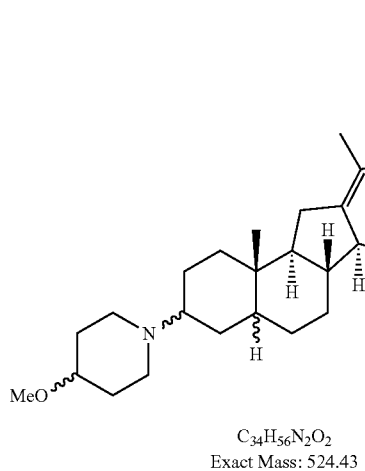

2b

C₃₄H₅₆N₂O₂
Exact Mass: 524.43

2c

C₃₄H₅₆N₂O
Exact Mass: 508.44

In order to study side-product formation, experiments were carried out as described in Example 2 above, using Compound 1 as substrate and Degussa type E101 10% palladium on carbon as catalyst, while varying the solvent and extending the reaction time. The results are summarized in Table 7 below (percentages determined by HPLC).

TABLE 7

| Solvent | % Side-product at 17 h. | % Side-product at 65 h. |
|---|---|---|
| 3-Picoline | 2 | 12 |
| 10% 3-Picoline in THF | 6 | 26 |
| 4-OMePy | 1 | 3 |
| Pyridine | 13 | 37 |

Example 7

Reduction of Compound 1

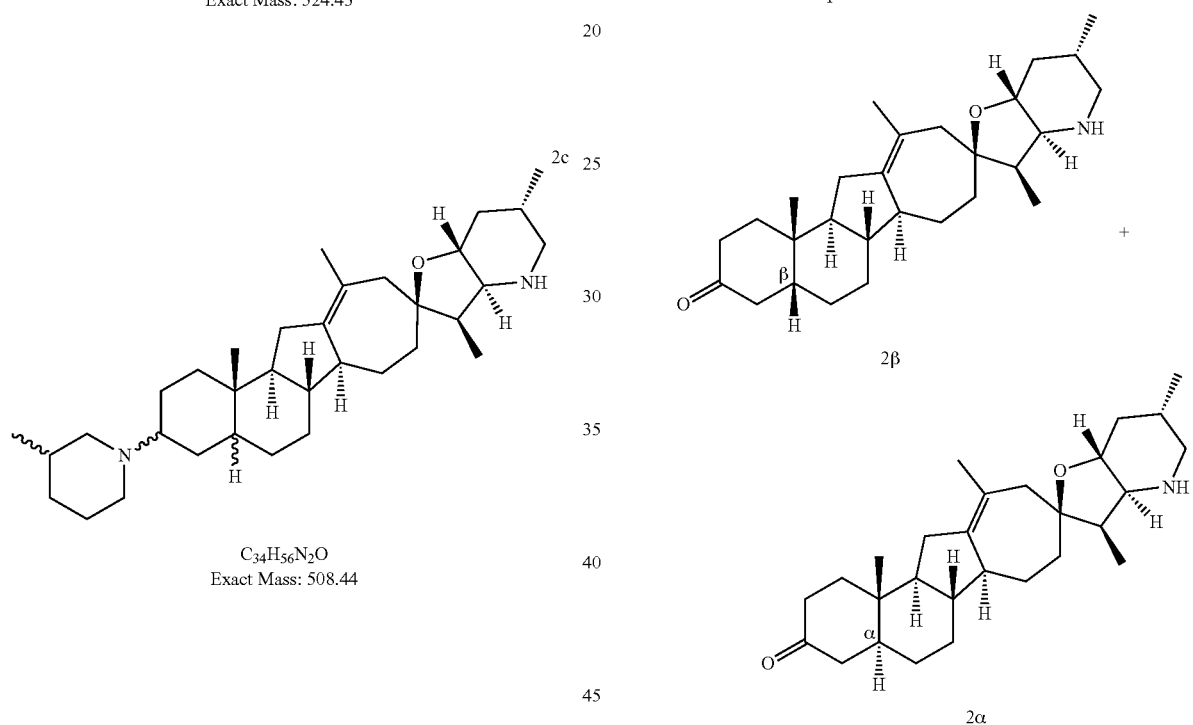

Compound 1 (459 mg) and Johnson-Matthey 5% palladium on carbon (A503023-5, 101 mg) were charged to an appropriately sized multi neck reaction vessel. The vessel was purged with nitrogen, then 3-picoline (2.2 g) was charged as the solvent. Stirring was started and the vessel was first degassed using nitrogen and then stirred under hydrogen at atmospheric pressure for 8 hours. At the end of the reaction, the catalyst was removed by filtration through 0.2 micron media, rinsing with ACN (1.4 ml). The filtrate and rinse were combined in a clean reaction vessel equipped with mechanical stirring, an internal temperature probe, and a nitrogen atmosphere.

A solution of citric acid (3.7 g) in water (9.2 ml) was charged to the reaction vessel at or below 30° C., and the reduced compound was allowed to slowly crystallize from solution as the citrate salt at 20° C. and then 0° C. The crystalline product was recovered by suction filtration and washed with water (3.7 ml). After drying, the citrate salt was isolated as a hydrate (3-5 wt % water) in 89.5% yield (622 mg) with a β/α ratio of 90:1. The citrate salt maintained its white color on storage at ambient temperature.

Example 8

Alternate Reduction of Compound 1

Compound 1 (20 g) was treated with balloon-pressure hydrogen gas in the presence of Johnson-Matthey 5% palladium on carbon (A503023-5, 4 g) in 3-picoline (200 mL), as described herein. When the reaction was judged complete after 7.5 hours, the catalyst was removed by filtration and the flask and filtration media were rinsed with THF (2×50 mL). The solution was concentrated to remove the THF, and 3N HCl (440 mL) at 5° C. was added. The filtrate-containing flask was rinsed with a solution of THF (20 mL) and water (20 mL) and the pH of the mixture was adjusted to 2.0 with 3N HCl. Water (200 mL) was added, and a white precipitate formed. The solid was transferred to a beaker and methyl t-butyl ether (400 mL) and saturated aqueous NaHCO3 (400 mL) were added. The organic layer was collected and filtered, and the aqueous layer was extracted with methyl t-butyl ether (2×100 mL). The combined organic layer was washed with water (2×200 mL), dried over anhydrous sodium sulfate and filtered. The filtrate was concentrated to yield the solid free-base product (17.42 g, 87%) with a β/α ratio of 76:1.

Example 9

Salt Formation

A. Synthesis of Reduced Product

Compound 1 (30.0 g) and Johnson-Matthey 5% palladium on carbon (A503023-5, 6.0 g) were charged to a 3000 mL round bottom flask, and 3-picoline (150 mL) was added. Stirring was started and the flask was degassed under vacuum and the charged with nitrogen three times. The flask was kept under balloon-pressure hydrogen atmosphere with stirring for 8 h. HPLC indicated that the reaction was not complete, so an additional 0.1 g of catalyst was added and the reaction was stirred under hydrogen for another 1.5 h. The catalyst was removed by filtration and the filtrate (164 g) was divided into portions for the salting study.

B. HCl Salt Formation

To 5.5 g of the filtrate was added acetonitrile (3.0 g). Hydrochloric acid (17 mL of 3N aqueous solution) was added. The pH of the solution was found to be 1.0. Water (10 g) was added and the mixture was stirred for 1.5 h. The solid precipitate was filtered (filtration time 2 min. 52 sec.) and dried to yield 0.95 g (87%) of a white solid. The salt turned slightly pink on storage at ambient temperature.

C. HBr Salt Formation

To 5.5 g of the filtrate was added acetonitrile (3.0 g). Hydrobromic acid (28 mL of 3N aqueous solution) was added. The pH of the solution was found to be 4.7. The mixture was stirred for 1.5 h. The solid precipitate was filtered (filtration time 1 min. 20 sec.) and dried to yield 0.97 g (82%) of a white solid. The salt turned light brown to black on storage at ambient temperature.

D. H₂SO₄ Salt Formation

To 5.5 g of the filtrate was added acetonitrile (3.0 g). Sulfuric acid (11 mL of 3N aqueous solution) was added. The pH of the solution was found to be 1.5. Water (16 g) and sodium chloride (1.0 g) were added and the mixture was stirred until a solid precipitate formed. The solid was filtered (filtration time 3 min. 23 sec.) and dried to yield 1.2 g (97%) of a white solid. The salt turned slightly pink on storage at ambient temperature.

E. Methanesulfonate Salt Formation

To 5.5 g of the filtrate was added acetonitrile (3.0 g). Methansulfonic acid (17 mL of 3N aqueous solution) was added. The pH of the solution was found to be 1.5. Water (10 g) and sodium bromide (1.73 g) were added and the mixture was stirred until a solid precipitate formed. The solid was filtered (filtration time 2 min. 35 sec.) and dried to yield 1.1 g (83%) of a white solid. The salt turned slightly pink on storage at ambient temperature.

The results of the various salt-producing experiments described in Examples 7 and 9 are summarized in Table 8 below.

TABLE 8

| Salt | % Yield | Appearance after storage |
| --- | --- | --- |
| Citrate | 89.5 | White |
| HCl | 87 | Pink |
| HBr | 82 | Brown/black |
| H₂SO₄ | 97 | Pink |
| Methanesulfonate | 83 | Pink |

Example 10

Synthesis of Compound 42

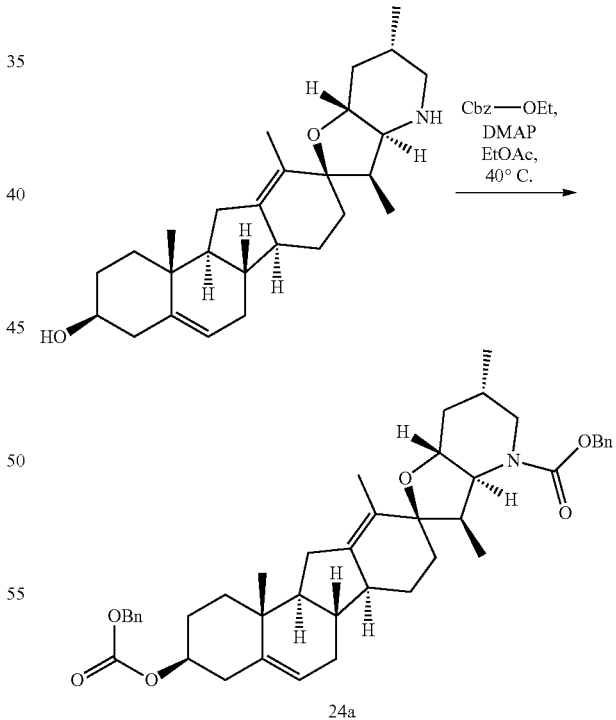

Recrystallized cyclopamine (2.07 g) was charged to an appropriately sized reaction vessel and placed under an inert atmosphere. EtOAc (7.6 g), triethylamine (1.53 g), and DMAP (307 mg) were added sequentially. The suspension was warmed to 40° C. Cbz-OBt was added in three portions over 90 minutes, keeping the internal temperature below 45°

C. The reaction mixture was stirred at 40° C. for 90 minutes. The temperature was maintained while methanol (26.4 g) was slowly added to the reaction mixture. The resulting suspension was cooled to room temperature and stirred for at least 15 hours. The crude product was collected by filtration and rinsed with methanol (5 g). The white solid was dried under vacuum to a constant weight and recrystallized from heptane (30.3 g) and toluene (3.2 g) to afford Compound 24a (3.0 g).

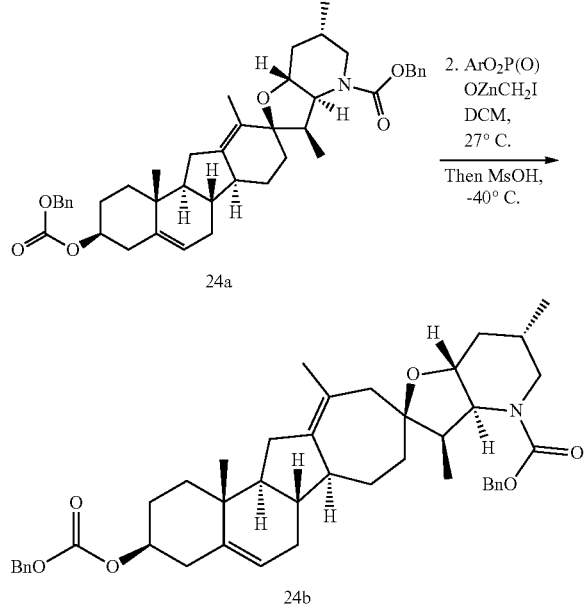

Solid bis(2,6-dimethylphenyl)hydrogenphosphate and 24a were pre-dried and placed under a nitrogen atmosphere. Neat diethyl zinc (722 mg) was charged to an appropriately sized reaction vessel containing DCM (9.0 g). DCM solutions of the phosphate (1.83 g in 17.9 g) and IPI-332690 (1.34 g in 3.6 g) were added sequentially at or below 25° C. Diiodomethane (1.58 g) was charged and the reaction was stirred at 28° C. for 4-6 hours. The reaction was cooled to −45° C. and a solution of methanesulfonic acid in DCM (566 mg in 1.5 g) was charged. After 15 minutes, morpholine (1.711 g) was added and the mixture was allowed to warm to room temperature overnight. The organic layer was washed twice with 2N HCl (2×13.6 g) then sequentially with 4.8 wt % sodium carbonate (aq), 4.8 wt % sodium sulfite (aq), and 4.8 wt % brine (13.6 g each). The organic layer was dried, filtered, concentrated to 4 g and diluted with isopropanol (4 g). The product was crystallized from solution by the slow addition of methanol (9.3 g). Filtration with a methanol rinse (2.6 g) and drying afforded 1.09 g of 24b (79% isolated yield).

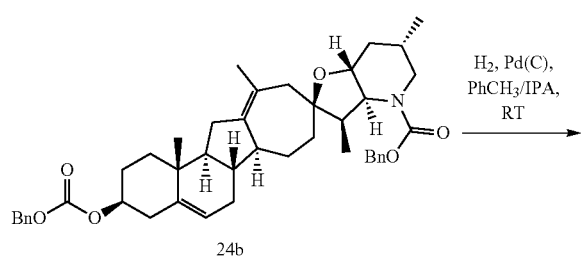

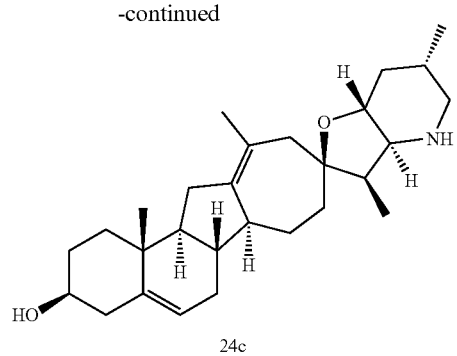

Johnson Matthey Pd/C catalyst A-305038-5 (890 mg) was charged to an appropriately sized reaction vessel, followed by 24b (2.24 g). The reaction vessel was purged with $N_2$ and toluene (21.8 g) and 2-propanol (6.7 g) were added sequentially. The system was degassed and placed under a nitrogen atmosphere, and the process was repeated with hydrogen. The system was stirred vigorously and the hydrogen blanket was maintained at one atmosphere for 4-5 hours. Ethylenediamine (12.9 mg) was charged and the mixture was stirred for 15 minutes. The catalyst was removed by filtration with a toluene:IPA (3:1) rinse. The filtrate and rinses were concentrated and solvent exchanged to toluene. The product was crystallized from toluene (19.0 g) and heptane (18.0 g) to afford 24c as a white crystalline solid (1.34 g, 98% yield).

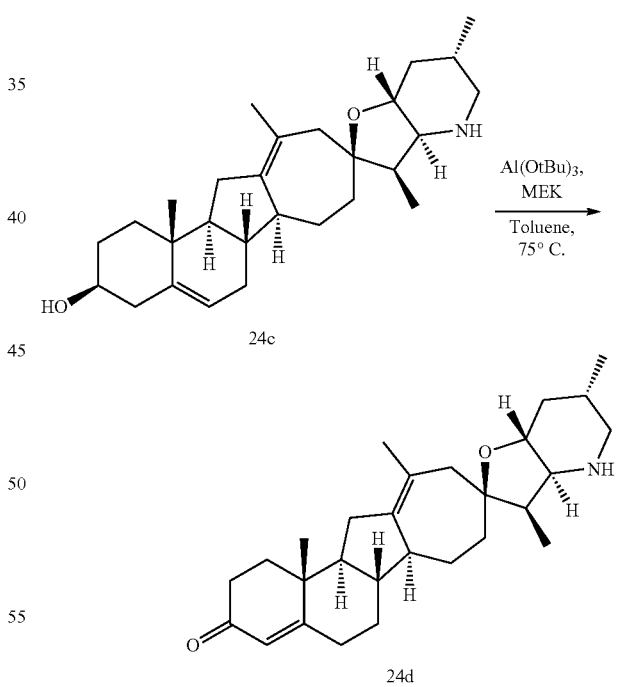

24c (644 mg) was charged to an appropriately sized reaction vessel followed by aluminum t-butoxide (525 mg), toluene (8.34 g, 15 vol), and 2-butanone (7.83 g, 15 vol). The contents of the flask were degassed with evacuation/nitrogen purge cycles to remove oxygen and the reaction mixture was heated at 75° C. with vigorous stirring for 16-18 hours. The reaction was quenched by the addition of aqueous Rochelle's salt (2.6 g in 10.3 g water) and the mixture was vigorously stirred for one hour at 45° C. The aqueous and organic layers were separated. The aqueous layer was back extracted with a mixture of toluene (2.9 g) and EtOAc (2.9 g). The organic layers were combined and washed with fresh Rochelle's salt solution (2.6 g in 10.3 g water) and then with water (12.9 g). The resulting organic layer was dried over sodium sulfate (1.97 g), filtered, and concentrated in vacuo. The product was crystallized via a charge and concentration solvent exchange first to IPA (6.5 g) and then heptane (7.7 g). The thick heptane slurry (~2.7 g) was stirred overnight and solids were collected by filtration. Vacuum drying afforded 24d (550 mg) in an 85% yield.

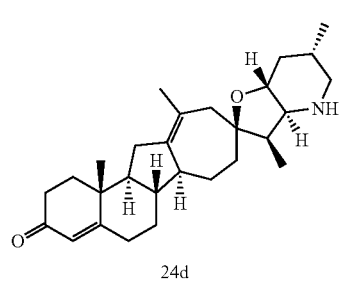

24d

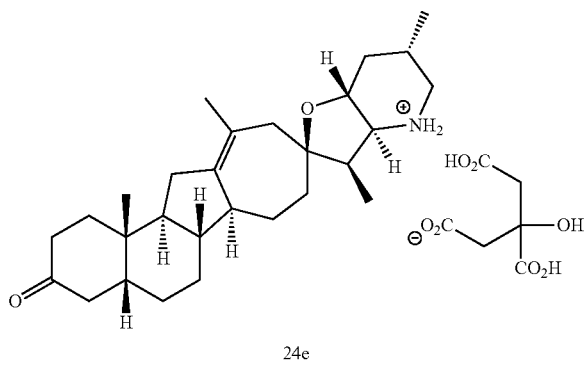

24e

The enone 24d (459 mg) and Johnson-Matthey 5% palladium on carbon (A503023-5, 101 mg) were charged to an appropriately sized multi neck reaction vessel. The vessel was purged with nitrogen and 3-picoline (2.2 g) was charged as the solvent. Stirring was started and the vessel was first degassed using nitrogen and then stirred under hydrogen at atmospheric pressure for 8 hours. At the end of the reaction, the catalyst was removed by filtration through 0.2 micron media, rinsing with ACN (1.4 ml). The filtrate and rinse were combined in a clean reaction vessel equipped with mechanical stirring, an internal temperature probe, and a nitrogen atmosphere. A solution of citric acid (3.7 g) in water (9.2 ml) was charged to the reaction vessel at or below 30° C., and the product was allowed to slowly crystallize from solution as the citrate salt at 20° C. and then 0° C. The crystalline product was recovered by suction filtration and washed with water (3.7 ml). After drying, the citrate salt, 24e, was isolated as a hydrate (3-5 wt % water) in 89.5% yield (622 mg) with a β:α ratio approaching 90:1.

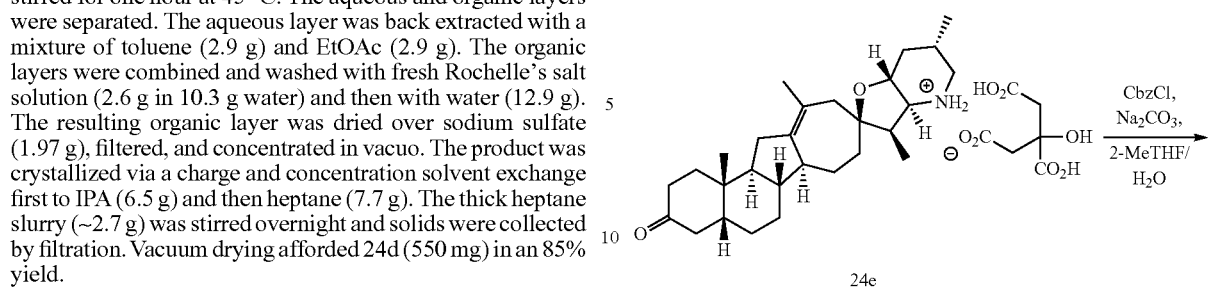

24e 24e (1.50 g) was charged to the appropriately sized reactor along with 2-methyltetrahydrofuran (7.7 g) and 1M sodium carbonate (9.0 ml). A solution of benzyl chloroformate (454 mg) in 2-methyltetrahydrofuran (300 mg) was added via addition funnel and the reaction was stirred at ambient temperature for 1-2 hours. When the reaction was complete, the stirring was stopped, the layers were separated and the organic layer was washed twice with water (2×6 g). The organic layer was dried over sodium sulfate (3 g), filtered and concentrated. Residual water was reduced further by concentration from fresh 2-methyltetrahydrofuran (6.5 g) and the material was transferred as solution in anhydrous 2-methyltetrahydrofuran to the next reaction.

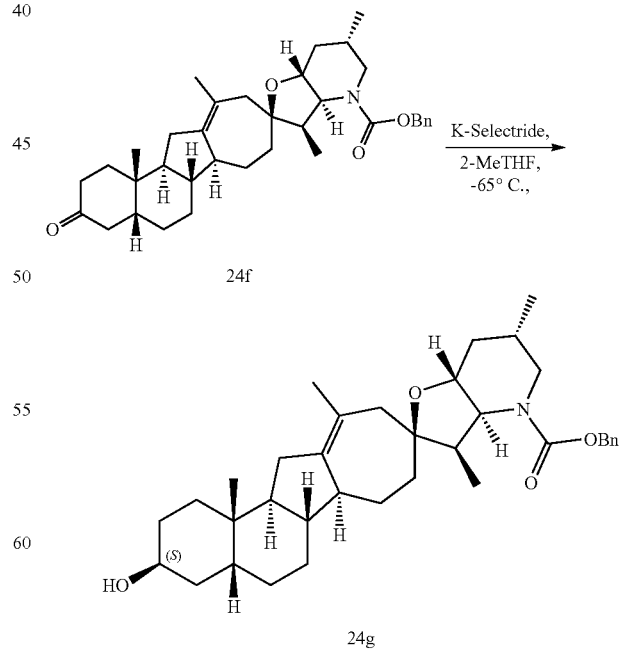

Commercial 1 M K-Selectride® in THF (1.20 g) was charged to a dry reaction vessel under a nitrogen atmosphere, diluted with anhydrous 2-methyltetrahydrofuran (2.10 g) and cooled to −65° C. The solution of 24f (0.41 g) in 2-methyltetrahydrofuran (1.5 g) was then slowly added to the reaction vessel to control the internal temperature at −65 ±5° C. The reaction was stirred for 2 hours and warmed to −20° C. over approximately 1 hour and stirred for an additional hour. The reaction was quenched at low temperature with MeOH (0.33 g). The reagent was destroyed by the sequential addition of 3M NaOH (2.4 g) at −20° C. and 15% hydrogen peroxide in water (1.04 g) at or below 5° C., then the reaction was stirred overnight at ambient temperatures. The layers were separated and the organic layer was washed sequentially with 1M aqueous NaOH (2 ml), 0.5 M aqueous Na$_2$SO$_3$ (2 ml), and water (2 ml) adjusted to a pH of 3 with HCl. The organic layer was dried over sodium sulfate (0.82 g), filtered and concentrated. The product 24 g (0.457 g) was re-concentrated from DCM (0.9 g) and used in the next reaction.

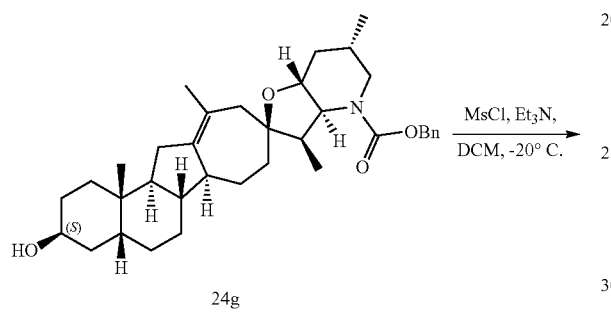

24g 24 g (1.36 g) was charged with anhydrous DCM (18.1 g) to an appropriately size reaction vessel, place under an inert atmosphere and cooled to −20° C. Triethylamine (0.61 mg) was charged followed by the slow addition of methanesulfonyl chloride (373 mg) in anhydrous DCM (300 mg). The reaction was stirred for 1 hour at −20° C. When complete, the reaction was quenched with water (13.6 g) and allowed to warm. The layers were separated and the organic layer was washed with 2.5 wt % sodium bicarbonate (13.8 g) and then water (10.9 g). The organic layer was dried over sodium sulfate (4 g), filtered, and concentrated. The product solution was solvent exchanged via charge and concentration to t-butyl methyl ether (10.9 ml) and then 1,3-dimethyl-3,4,5,6-tetrahydro-2(1H)-pyrimidinone (DMPU, 4.7 ml). The DMPU solution was used directly in the next reaction.

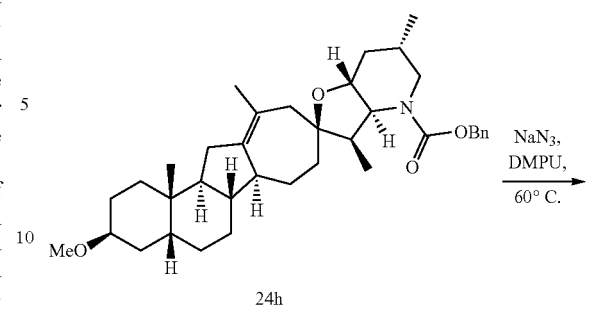

24h

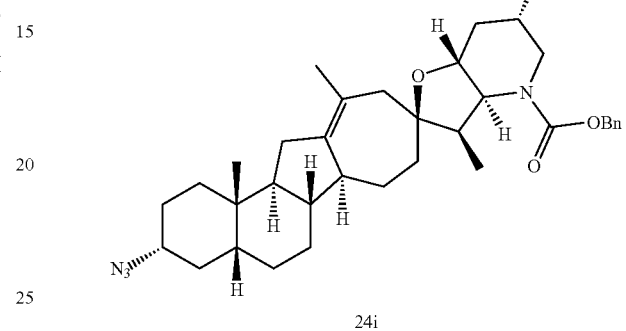

24i

Sodium azide (0.74 g) was charged to an appropriately sized reaction vessel. The solution of 24 h (1.46 g) in DMPU (5.9 g) was charged to the reaction vessel, rinsing with additional DMPU (1.9 g). The suspension was heated to 60° C. for 15 hours, maintaining a nitrogen sweep for the entire reaction. The reaction was cooled to ambient temperature and diluted with MTBE (11.7 g). The organic solution was washed 3 times with 2% saline (3×8 g), dried over sodium sulfate (4.4 g), filtered, and concentrated. The product was concentrated from THF (6.4 g) and used directly in the next reaction.

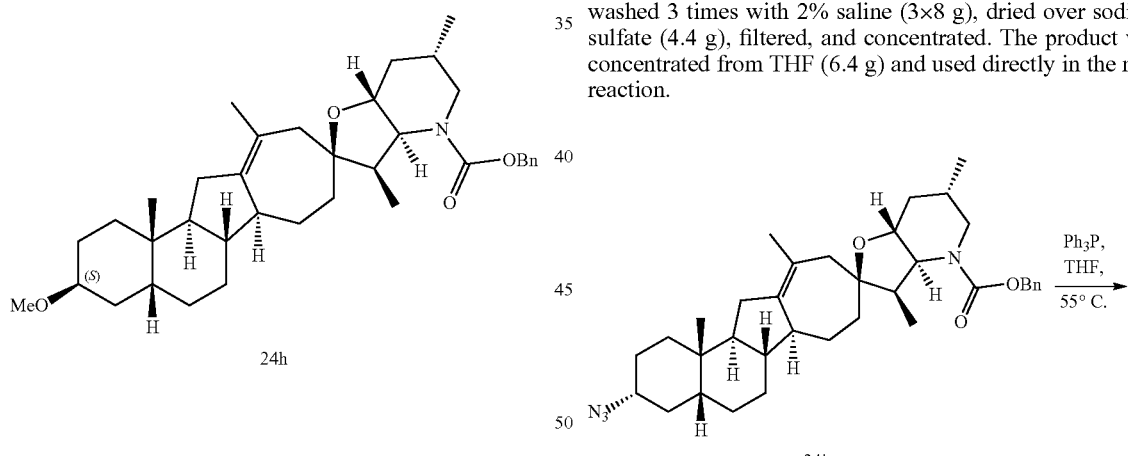

24i

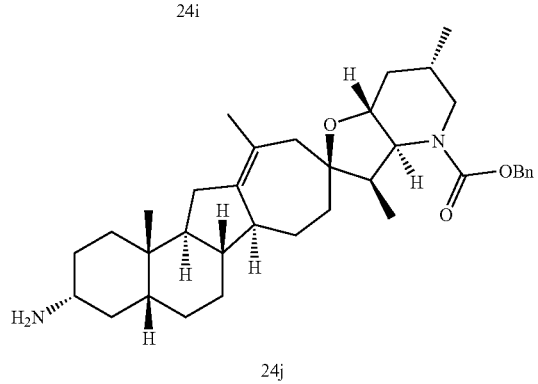

24j

The crude 24i (1.34 g) was dissolved and transferred to a suitably sized reaction vessel with THF (12.6 g). Triphenylphosphine (0.70 g) and water (0.44 g) were charged and the reaction is heated to 55° C. for 15-24 hours. When complete, the reaction was cooled to ambient temperature, dried with magnesium sulfate (1.4 g), filtered and concentrated. The solids were dissolved and concentrated from three portions of DCM (3×9 g) and purified by silica gel chromatography using DCM/MeOH/Et$_3$N gradients to remove reagent based impurities. The pooled fractions were concentrated to dryness, dissolved in DCM (6.8 g) and concentrated to dryness again to afford an amorphous solid (1.12 g) which was used in the next reaction.

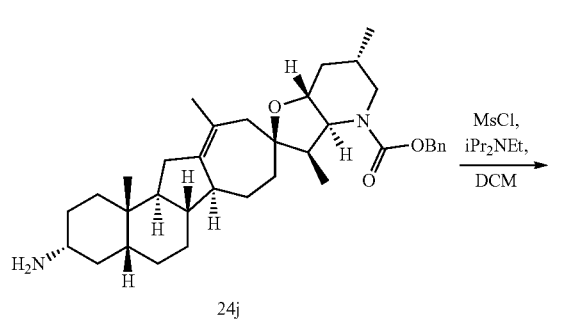

24j 24j (1.09 g) was dissolved and transferred to an appropriately sized reaction vessel with anhydrous DCM (15.8 g) and placed under a nitrogen atmosphere. The solution was cooled to 0° C. Diisopropylethylamine (357 mg) and neat methanesulfonyl chloride (0.165 ml) were charged sequentially while maintaining temperature between below 5° C. The reaction was quenched with 0.4 M aqueous sodium bicarbonate (11.4 g) and warmed to ambient temperature. The layers were separated and the aqueous phase was back extracted with DCM (5.8 g). The combined organic layers were dried over magnesium sulfate (0.55 g), filtered and concentrated. The product 24k was dissolved and striped from 2-propanol (4.0 g) to remove residual DCM and used directly in the next reaction.

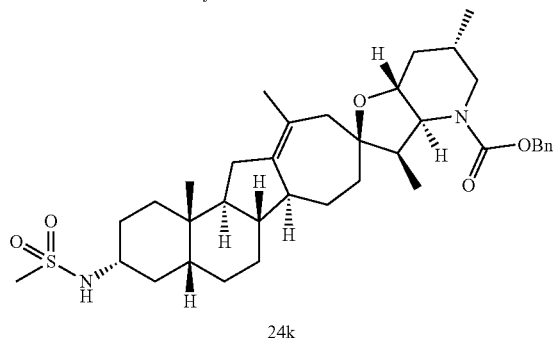

24k

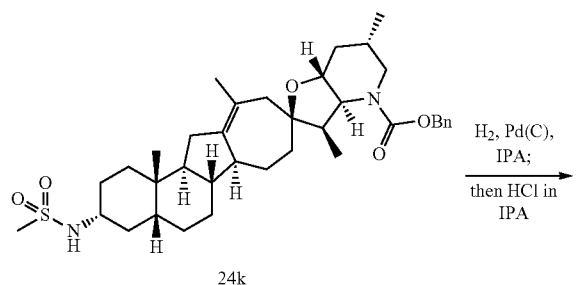

24k

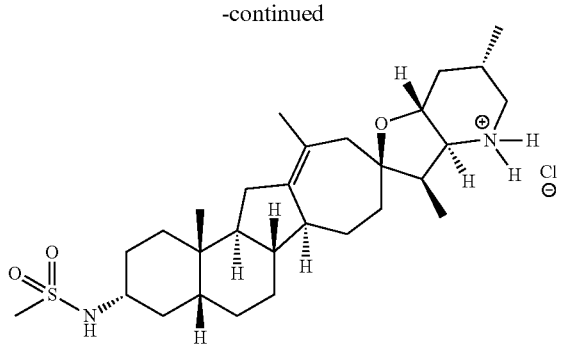

42

Aldrich Degussa type E101 NE/W 10% Pd/C (249 mg) was charged to an appropriately sized reaction vessel and placed under a nitrogen atmosphere. A 2-propanol (9.8 g) solution of 24k (1.24 g) was charged to the reaction vessel. The system was degassed and placed under a nitrogen atmosphere, and the process was repeated with hydrogen. The reaction was stirred under 1 atm of hydrogen at ambient temperature for 8 hours. An inert atmosphere was returned to the vessel and a second charge of catalyst (125 mg) slurried in 2-propanol (0.5 g) was added to the reaction. The reaction mixture was degassed and placed under a nitrogen atmosphere, and the process was repeated with hydrogen. The reaction was stirred under 1 atm of hydrogen for another 15 hours at ambient temperature. When complete, the reaction was filtered, treated with steam activated carbon (200 mg), and filtered again. The solution was dried by partial concentration transferred to a reaction vessel and diluted with anhydrous 2-propanol to 0.09 M based on the theoretical yield. A 1.25 M HCl solution in 2-propanol (1.64 g) was charged over 20 minutes. The hydrochloride salt crystallizes slowly with gentle stirring and was isolated by filtration. The crystals were washed with 2-propanol (2.5 g) and vacuum dried to afford Compound 42 (916 mg, 80% yield) as a 1:1 IPA solvate.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of reducing the C—C double bond of an enone of a steroidal compound to produce a mixture of β ketone product and α ketone product, the method comprising treating a solution or suspension of the steroidal compound in a solvent with hydrogen gas in the presence of a catalyst and a substituted pyridine.

2. The method of claim 1, wherein an excess of the β ketone product is produced compared to the α ketone product.

3. The method of claim 1, wherein the ratio of the β ketone product to the α ketone product is at least 2:1.

4. The method of claim 1, wherein the ratio of the β ketone product to the α ketone product is at least 10:1.

5. The method of claim 1, wherein the ratio of the β ketone product to the α ketone product is at least 20:1.

6. The method of claim 1, wherein the ratio of the β ketone product to the α ketone product is at least 50:1.

7. The method of claim 1, wherein the substituted pyridine is a 3-substituted pyridine.

8. The method of claim 7, wherein the 3-substituted pyridine is selected from 3-picoline, 3-methoxypyridine, 3-ethylpyridine, 3-n-butylpyridine, 3-isobutylpyridine, 3-hydroxypyridine, 3-aminopyridine, and 3-dimethylaminopyridine.

9. The method of claim 7, wherein the 3-substituted pyridine is 3-picoline.

10. The method of claim 1, wherein the catalyst is a palladium catalyst.

11. The method of claim 1, wherein the solvent comprises the substituted pyridine.

12. The method of claim 11, wherein the solvent comprises 3-picoline.

13. A method of making a mixture of compounds of formulae II and III:

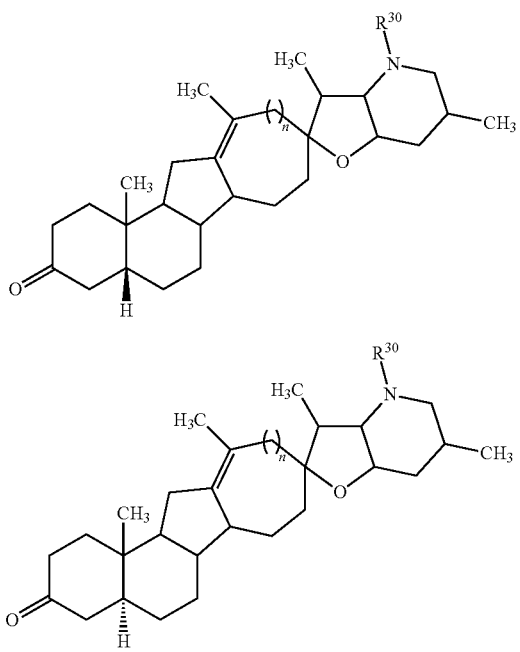

or a pharmaceutically acceptable salt thereof, wherein:
n is 0 or 1;
$R^{30}$ is H, alkyl, alkenyl, alkynyl, aryl, cycloalkyl, heterocycloalkyl, aralkyl, heteroaryl, heteroaralkyl, haloalkyl, $-OR^{31}$, $-C(O)R^{31}$, $-CO_2R^{31}$, $-SO_2R^{31}$, $-C(O)N(R^{31})(R^{31})$, $-[C(R)_2]_q-R^{31}$, $-[(W)-N(R)C(O)]_qR^{31}$, $-[(W)-C(O)]_qR^{31}$, $-[(W)-C(O)O]_qR^{31}$, $-[(W)-OC(O)]_qR^3$, $-[(W)-SO_2]_qR^{31}$, $-[(W)N(R^{31})SO_2]_qR^{31}$, $-[(W)-C(O)N(R^{31})]_qR^{31}$, $-[(W)-O]_qR^{31}$, $-[(W)-N(R)]_qR^{31}$, $-W-(NR^{31})_3{}^+X^-$ or $-[(W)-S]_qR^{31}$;
W, at each occurrence, independently is an alkylene group;
q, at each occurrence, independently is 1, 2, 3, 4, 5, or 6;
$X^-$ is a halide;
$R^{31}$, at each occurrence, independently is H, alkyl, alkenyl, alkynyl, aryl, cycloalkyl, heterocycloalkyl, aralkyl, heteroaryl, heteroaralkyl or $-[C(R)_2]_p-R^{32}$;
or any two occurrences of $R^{31}$ taken together with the atom to which they are bound form an optionally substituted 4-8 membered ring that contains 0-3 heteroatoms selected from N, O and S;
p is 0-6;
each $R^{32}$ is independently
hydroxyl, $-N(R)COR$, $-N(R)C(O)OR$, $-N(R)SO_2(R)$, $-C(O)N(R)_2$, $-OC(O)N(R)(R)$, $-SO_2N(R)(R)$, $-N(R)(R)$, $-COOR$, $-C(O)N(OH)(R)$, $-OS(O)_2OR$, $-S(O)_2OR$, $-OP(O)(OR)(OR)$, $-NP(O)(OR)(OR)$, or $-P(O)(OR)(OR)$; and each R is independently H, alkyl, alkenyl, alkynyl, aryl, cycloalkyl or aralkyl;

the method comprising treating a solution or suspension of compound of formula IV:

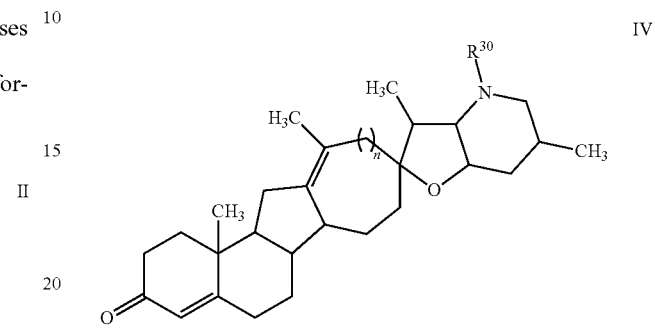

or a pharmaceutically acceptable salt thereof, in a solvent with hydrogen gas in the presence of a catalyst and a substituted pyridine.

14. The method of claim 13, wherein an excess of the compound of formula II is produced compared to the compound of formula III.

15. The method of claim 13, wherein the ratio of the compound of formula II to compound of formula III is at least 10:1.

16. The method of claim 13, wherein the ratio of the compound of formula II to compound of formula III is at least 20:1.

17. The method of claim 13, wherein the substituted pyridine is a 3-substituted pyridine.

18. The method of claim 17, wherein the 3-substituted pyridine is 3-picoline.

19. The method of claim 13, wherein the solvent comprises the substituted pyridine.

20. The method of claim 19, wherein the solvent comprises 3-picoline.

21. The method of claim 13, wherein the catalyst is a palladium catalyst.

22. The method of claim 13, wherein n is 1.

23. The method of claim 22, wherein $R^{30}$ is H.

24. The method of claim 13, wherein the compounds of formulae II and III have the following absolute chemistry:

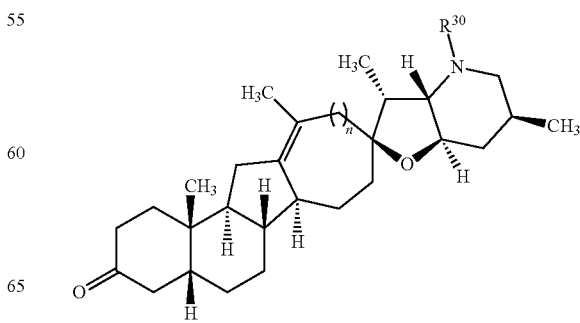

-continued
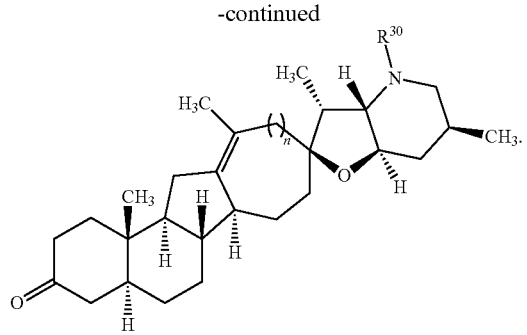
* * * * *